(12) United States Patent
Morimoto et al.

(10) Patent No.: US 12,310,554 B2
(45) Date of Patent: May 27, 2025

(54) ENDOSCOPE HAVING ELEVATOR SUPPORT MEMBER IN DISTAL END PORTION BODY FOR HEAT DISSIPATION

(71) Applicant: FUJIFILM Corporation, Tokyo (JP)

(72) Inventors: Yasuhiko Morimoto, Kanagawa (JP); Shozo Iyama, Kanagawa (JP); Tsuneo Fukuzawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1106 days.

(21) Appl. No.: 17/179,346

(22) Filed: Feb. 18, 2021

(65) Prior Publication Data

US 2021/0169312 A1    Jun. 10, 2021

Related U.S. Application Data

(63) Continuation of application No. PCT/JP2019/033256, filed on Aug. 26, 2019.

(30) Foreign Application Priority Data

Sep. 10, 2018    (JP) .................................. 2018-169148

(51) Int. Cl.
*A61B 1/00*    (2006.01)
*A61B 1/005*    (2006.01)
(Continued)

(52) U.S. Cl.
CPC ...... *A61B 1/00098* (2013.01); *A61B 1/00091* (2013.01); *A61B 1/00096* (2013.01);
(Continued)

(58) Field of Classification Search
CPC .. A61B 8/445; A61B 8/12; A61B 1/07; A61B 1/018; A61B 1/00137;
(Continued)

(56) References Cited

U.S. PATENT DOCUMENTS 4,760,840 A * 8/1988 Fournier, Jr. .......... A61B 18/24
600/173
4,867,138 A * 9/1989 Kubota .............. A61B 1/00098
600/105
(Continued)

FOREIGN PATENT DOCUMENTS

JP    2003153852    5/2003
JP    2014128465    7/2014
(Continued)

OTHER PUBLICATIONS

"International Search Report (Form PCT/ISA/210) of PCT/JP2019/033256," mailed on Oct. 8, 2019, with English translation thereof, pp. 1-3.

(Continued)

*Primary Examiner* — Anh Tuan T Nguyen
*Assistant Examiner* — Shankar Raj Ghimire
(74) *Attorney, Agent, or Firm* — JCIPRNET

(57) ABSTRACT

Provided is an endoscope that can suppress increase in the temperature of a distal end portion of an insertion section while preventing increase in the number of components and increase in the diameter of the distal end portion. An endoscope includes: a distal end portion body that is provided on a distal end side of an insertion section and that has a distal end, a proximal end, and a longitudinal axis; a treatment tool lead-out port that is formed in the distal end portion body and that leads out a treatment tool inserted through an inside of the insertion section; an elevator support member that is provided in the distal end portion body, that is made of a metal, and that rotatably supports an elevator that controls a lead-out direction in which the treatment tool is led out from the treatment tool lead-out port; a light guide that is inserted through the inside of the insertion section and that emits illumination light through an illumination window formed in the distal end portion body;

(Continued)

and a light guide holding portion that is provided in the elevator support member and that holds a light guide distal end portion of the light guide on the illumination window side.

10 Claims, 16 Drawing Sheets

(51) Int. Cl.
    *A61B 1/018*     (2006.01)
    *A61B 1/06*     (2006.01)
    *A61B 1/07*     (2006.01)
    *A61B 8/00*     (2006.01)
    *A61B 8/12*     (2006.01)
    *A61B 1/015*     (2006.01)

(52) U.S. Cl.
    CPC .......... *A61B 1/00137* (2013.01); *A61B 1/005* (2013.01); *A61B 1/018* (2013.01); *A61B 1/0625* (2022.02); *A61B 1/07* (2013.01); *A61B 8/12* (2013.01); *A61B 8/445* (2013.01); *A61B 1/015* (2013.01)

(58) Field of Classification Search
    CPC ............ A61B 1/00096; A61B 1/00091; A61B 1/0625; A61B 1/00098
    See application file for complete search history.

(56) References Cited

U.S. PATENT DOCUMENTS

| | | | | |
|---|---|---|---|---|
| 6,238,336 | B1* | 5/2001 | Ouchi | A61B 8/12 600/463 |
| 6,390,973 | B1* | 5/2002 | Ouchi | A61B 1/00177 600/463 |
| 6,458,074 | B1* | 10/2002 | Matsui | A61B 1/018 600/106 |
| 6,461,304 | B1* | 10/2002 | Tanaka | A61B 8/4488 600/462 |
| 7,318,806 | B2* | 1/2008 | Kohno | A61B 8/12 600/463 |
| 7,771,349 | B2* | 8/2010 | Kohno | A61B 8/12 600/106 |
| 10,806,338 | B2* | 10/2020 | Morimoto | A61B 1/018 |
| 2002/0091303 | A1* | 7/2002 | Ootawara | A61B 1/01 600/106 |
| 2003/0040657 | A1* | 2/2003 | Yamaya | A61B 1/0052 600/106 |
| 2004/0049095 | A1* | 3/2004 | Goto | A61B 1/00098 600/107 |
| 2005/0222493 | A1* | 10/2005 | Kohno | A61B 1/00098 600/117 |
| 2005/0228289 | A1* | 10/2005 | Kohno | A61B 1/018 600/463 |
| 2006/0235271 | A1* | 10/2006 | Carter | A61B 1/00098 600/107 |
| 2007/0208219 | A1* | 9/2007 | Carter | A61B 1/018 600/107 |
| 2009/0054727 | A1* | 2/2009 | Yamaya | G02B 23/2469 600/107 |
| 2013/0331696 | A1* | 12/2013 | Morimoto | A61B 8/12 600/439 |
| 2015/0148598 | A1* | 5/2015 | Fukushima | A61B 1/00098 600/109 |
| 2016/0089003 | A1* | 3/2016 | Morimoto | A61B 1/00177 600/107 |
| 2016/0089125 | A1* | 3/2016 | Morimoto | A61B 1/00098 600/107 |
| 2016/0270630 | A1* | 9/2016 | Tanaka | A61B 1/00098 |
| 2016/0270633 | A1* | 9/2016 | Iwasaka | A61B 1/00098 |
| 2016/0270634 | A1* | 9/2016 | Tanaka | A61B 1/00098 |
| 2016/0270635 | A1* | 9/2016 | Tanaka | A61B 1/00098 |
| 2016/0270636 | A1* | 9/2016 | Iwasaka | A61B 1/00137 |
| 2016/0270637 | A1* | 9/2016 | Tanaka | A61B 1/00098 |
| 2016/0309993 | A1* | 10/2016 | Hosogoe | A61B 1/00071 |
| 2017/0014099 | A1* | 1/2017 | Morimoto | A61B 8/445 |
| 2017/0112362 | A1* | 4/2017 | Morimoto | A61B 1/00096 |
| 2017/0112363 | A1* | 4/2017 | Morimoto | A61B 1/0676 |
| 2017/0127920 | A1* | 5/2017 | Morimoto | A61B 1/00098 |
| 2017/0128043 | A1* | 5/2017 | Morimoto | A61B 1/0011 |
| 2017/0128044 | A1* | 5/2017 | Morimoto | G10K 11/30 |
| 2017/0290566 | A1* | 10/2017 | Hosogoe | A61B 1/018 |
| 2018/0092512 | A1* | 4/2018 | Hiraoka | A61B 1/00 |
| 2018/0235453 | A1* | 8/2018 | Morimoto | A61B 1/126 |
| 2018/0242832 | A1* | 8/2018 | Morimoto | A61B 1/00177 |
| 2019/0117045 | A1* | 4/2019 | Hosogoe | A61B 1/00137 |
| 2020/0315575 | A1* | 10/2020 | Morimoto | A61B 8/445 |
| 2020/0352418 | A1* | 11/2020 | Hayakawa | A61B 1/00098 |
| 2020/0352423 | A1* | 11/2020 | Hayakawa | A61B 1/00098 |
| 2021/0093162 | A1* | 4/2021 | Sueyasu | A61B 1/018 |
| 2022/0117468 | A1* | 4/2022 | Barry | A61B 1/00119 |
| 2022/0151480 | A1* | 5/2022 | Hansen | A61B 1/00165 |
| 2023/0126521 | A1* | 4/2023 | Isobe | A61B 1/00128 600/107 |
| 2023/0389780 | A1* | 12/2023 | Inoue | A61B 1/01 |

FOREIGN PATENT DOCUMENTS

| | | |
|---|---|---|
| JP | 2014132923 | 7/2014 |
| WO | 2018029103 | 2/2018 |

OTHER PUBLICATIONS

"Written Opinion of the International Searching Authority (Form PCT/ISA/237) of PCT/JP2019/033256," mailed on Oct. 8, 2019, with English translation thereof, pp. 1-6.

\* cited by examiner

ENDOSCOPE HAVING ELEVATOR SUPPORT MEMBER IN DISTAL END PORTION BODY FOR HEAT DISSIPATION

CROSS-REFERENCE TO RELATED APPLICATIONS

The present application is a Continuation of PCT International Application No. PCT/JP2019/033256 filed on Aug. 26, 2019 claiming priority under 35 U.S.C § 119(a) to Japanese Patent Application No. 2018-169148 filed on Sep. 10, 2018. Each of the above applications is hereby expressly incorporated by reference, in its entirety, into the present application.

BACKGROUND OF THE INVENTION

1. Field of the Invention

The present invention relates to an endoscope that includes a treatment tool lead-out port and an elevator on the distal end side of an insertion section.

2. Description of the Related Art

As an ultrasonic endoscope, an endoscope is known that includes an electron-scanning ultrasonic transducer in a distal end portion of an insertion section of the endoscope and in which a treatment tool lead-out port is disposed on the proximal end side of the ultrasonic transducer in the distal end portion. In an endoscopic inspection using the ultrasonic endoscope, for example, while acquiring an ultrasound image of a treatment target area (including an observation target area, an inspection area, and the like) by using the ultrasonic transducer, cells are sampled by inserting a puncture treatment tool, which has been led out to the inside of a body through a treatment tool insertion channel and a treatment tool lead-out port, into the treatment target area. In order to treat a desired position with such a treatment tool, it is necessary to change the lead-out direction in which the treatment tool is led out from the treatment tool lead-out port, which is formed in the distal end portion of the insertion section. Therefore, a treatment tool elevating mechanism is provided inside the treatment tool lead-out port of the distal end portion of the insertion section (see JP2014-132923A).

The treatment tool elevating mechanism includes an elevator housing chamber, an elevator, an elevator rotating mechanism, and the like. The elevator housing chamber is provided in the treatment tool lead-out port of the distal end portion of the insertion section. The elevator is supported so as to be rotatable around a rotational axis in the elevator housing chamber. The elevator rotating mechanism rotates the elevator in response to an elevator rotating operation performed on an operation section of the ultrasonic endoscope.

In an outer surface of the distal end portion of the insertion section, the treatment tool lead-out port, an observation window for observing a treatment target area, and, in addition, an illumination window that emits illumination light toward an treatment target area and the like are provided. Therefore, a light guide (optical fiber cable) that guides illumination light from a light source device to the illumination window is inserted through the inside of the insertion section.

A light guide distal end portion, which is a distal end portion of the light guide on a side facing the illumination window, generates heat by absorbing a part of illumination light. Therefore, the temperature of the distal end portion of the insertion section increases. JP2003-153852A discloses an endoscope apparatus in which, in a distal end portion of an insertion section, a region in which a light guide is fixed and the other region are separated and a heat insulator is provided at the boundary between these regions. Thus, increase in the temperature of the distal end portion of the insertion section due to generation of heat in the distal end portion is prevented.

SUMMARY OF THE INVENTION

JP2014-132923A does not describe suppression of increase in the temperature of the distal end portion of the insertion section due to generation of heat in the light guide distal end portion. When a heat insulator is provided in the distal end portion of the insertion section as in the endoscope apparatus described in JP2003-153852A, a problem arises in that the number of components of the distal end portion increases and the diameter of the distal end portion increases.

The present invention has been made against such a background, and an object thereof is to provide an endoscope that can suppress increase in the temperature of a distal end portion of an insertion section while preventing increase in the number of components and increase in the diameter of the distal end portion.

An endoscope for achieving the object of the present invention includes: a distal end portion body that is provided on a distal end side of an insertion section and that has a distal end, a proximal end, and a longitudinal axis; a treatment tool lead-out port that is formed in the distal end portion body and that leads out a treatment tool inserted through an inside of the insertion section; an elevator support member that is provided in the distal end portion body, that is made of a metal, and that rotatably supports an elevator that controls a lead-out direction in which the treatment tool is led out from the treatment tool lead-out port; a light guide that is inserted through the inside of the insertion section and that emits illumination light through an illumination window formed in the distal end portion body; and a light guide holding portion that is provided in the elevator support member and that holds a light guide distal end portion of the light guide on the illumination window side.

With the endoscope, it is possible to suppress increase in the temperature of the light guide distal end portion by transferring heat generated in the light guide distal end portion to the elevator support member made of a metal.

In an endoscope according to another aspect of the present invention, the light guide holding portion is a groove that is formed in an outer wall of the elevator support member and to which the light guide distal end portion is fitted. Thus, it is possible to transfer heat generated in the light guide distal end portion to the elevator support member.

In an endoscope according to another aspect of the present invention, the distal end portion body comprises an outer case including an outer case body and a cover, the outer case body has an opening portion and houses the elevator support member and the elevator in the opening portion, and the cover is removably attached to the opening portion and, when attached to the opening portion, presses the light guide distal end portion, which is fitted to the groove, against the groove and fixes the light guide distal end portion. Thus, the heat dissipation ability of the light guide distal end portion is improved, because the closeness of contact between the light guide distal end portion and the elevator support member is improved.

An endoscope according to another aspect of the present invention includes: an elevator housing chamber that is provided inside the treatment tool lead-out port of the distal end portion body and that houses the elevator; a treatment tool insertion channel that is provided in the insertion section and through which the treatment tool is inserted; a through hole that is formed in the elevator support member and that communicates with the elevator housing chamber; and a metal pipe that connects the treatment tool insertion channel and the through hole of the elevator support member. Thus, it is possible to further improve the heat dissipation ability of the light guide distal end portion, because it is possible to transfer heat generated in the light guide distal end portion further to the metal pipe via the elevator support member.

An endoscope according to another aspect of the present invention includes a bending portion that is connected to a proximal end side of the distal end portion body in the insertion section, the bending portion has a plurality of rings that are made of a metal and that are coupled along the longitudinal axis, and the elevator support member is connected directly or indirectly via another metal member to a distal end ring that is positioned on a most distal end side of the bending portion among the plurality of rings. Thus, it is possible to further improve the heat dissipation ability of the light guide distal end portion, because it is possible to transfer heat generated in the light guide distal end portion further to the ring made of a metal via the elevator support member.

An endoscope according to another aspect of the present invention includes an observation window that is provided in the distal end portion body and a nozzle that is provided in the distal end portion body and that ejects a fluid toward the observation window, and the illumination window is provided, in the distal end portion body, in an ejection range of the fluid ejected from the nozzle. Thus, it is possible to cool the light guide distal end portion via the illumination window by using a fluid ejected from the nozzle.

In an endoscope according to another aspect of the present invention, when a direction perpendicular to both of the longitudinal axis and a normal direction of an opening surface of the treatment tool lead-out port is defined as a width direction of the treatment tool lead-out port, the observation window is provided in the distal end portion body at a position on one side in the width direction relative to the treatment tool lead-out port, and the illumination window is provided in the distal end portion body at a position on the other side, which is opposite to the one side, relative to the treatment tool lead-out port.

In an endoscope according to another aspect of the present invention, the illumination window is a first illumination window that is provided in a proximal end side region that is positioned in the distal end portion body at a position shifted from the treatment tool lead-out port toward a proximal end side of the distal end portion body, and, when a direction perpendicular to both of the longitudinal axis and a normal direction of an opening surface of the treatment tool lead-out port is defined as a width direction of the treatment tool lead-out port, the observation window is provided in the distal end portion body at a position on one side in the width direction with respect to the proximal end side region.

In an endoscope according to another aspect of the present invention, the illumination window includes the first illumi-nation window and a second illumination window that is disposed in the distal end portion body at a position on the other side, which is opposite to the one side, with respect to the proximal end side region.

An endoscope according to another aspect of the present invention includes an ultrasonic transducer that is provided in the distal end portion body and that is positioned on a distal end side of the distal end portion body relative to the treatment tool lead-out port.

The present invention can suppress increase in the temperature of the distal end portion of the insertion section while preventing increase in the number of components and increase in the diameter of the distal end portion.

DESCRIPTION OF THE PREFERRED EMBODIMENTS

[Configuration of Ultrasonic Inspection System and Ultrasonic Endoscope]

Figure 1:
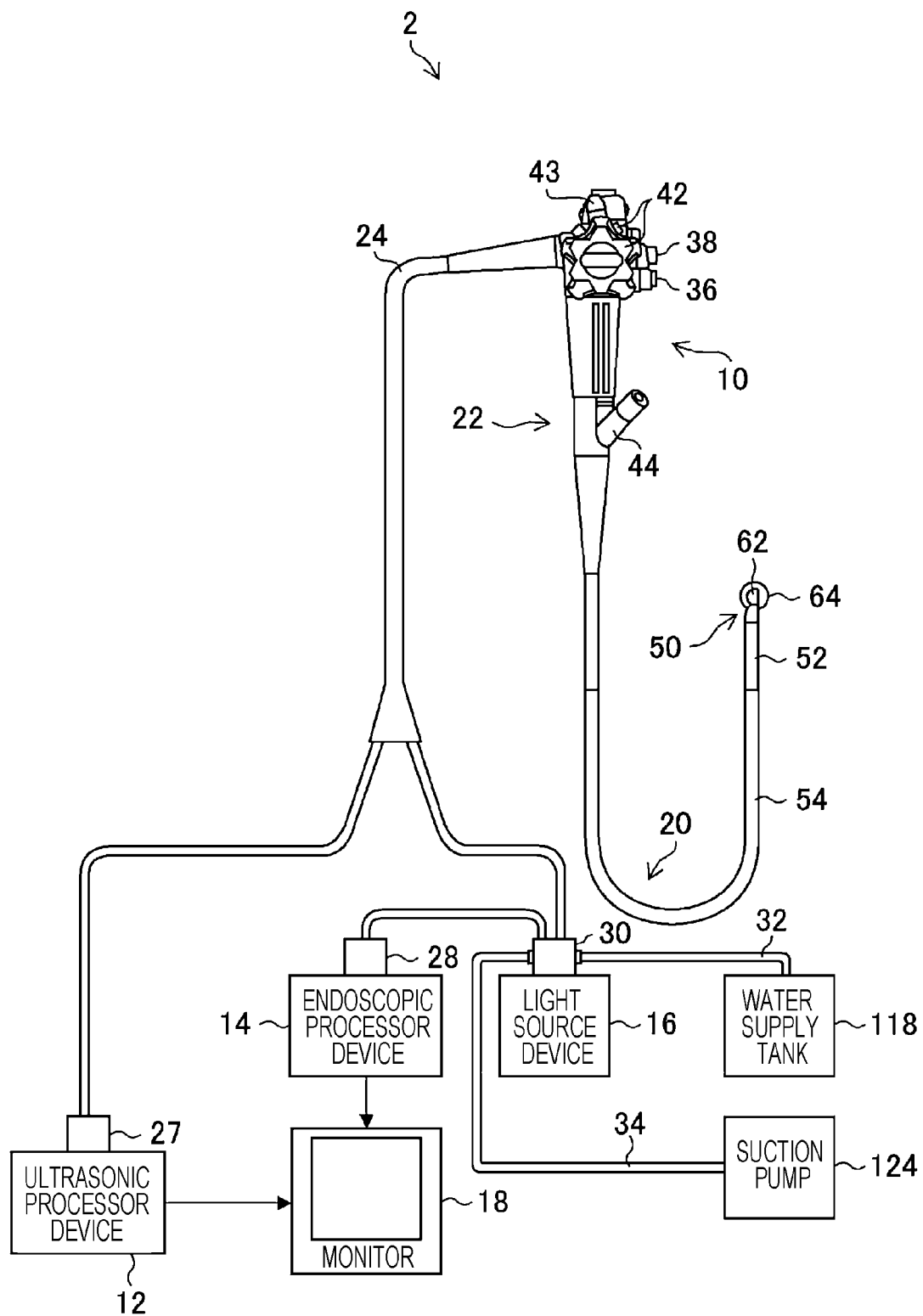
FIG. 1 is a schematic view of an ultrasonic inspection system to which an endoscope according to the present invention is applied.

FIG. 1 is a schematic view of an ultrasonic inspection system 2 to which an endoscope according to the present invention is applied. As illustrated in FIG. 1, the ultrasonic inspection system 2 includes an ultrasonic endoscope 10 that captures an image of the inside of a lumen 154 (also called a body cavity, see FIG. 12) of a subject to be examined, an ultrasonic processor device 12 that generates an ultrasound image, an endoscopic processor device 14 that generates an endoscopic image, a light source device 16 that supplies to the ultrasonic endoscope 10 illumination light for illuminating the inside of the lumen 154, and a monitor 18 that displays the ultrasound image and the endoscopic image.

The ultrasonic endoscope 10 corresponds to an endoscope according to the present invention and includes an insertion section 20, an operation section 22, and a universal cord 24.

The insertion section 20 is inserted into the lumen 154 (see FIG. 12) of various types. The operation section 22 is joined to the proximal end side of the insertion section 20 and receives an operation by an operator.

The operation section 22 is connected to one end side of the universal cord 24. On the other end side of the universal cord 24, an ultrasonic connector 27 connected to the ultrasonic processor device 12, an endoscopic connector 28 connected to the endoscopic processor device 14, and a light source connector 30 connected to the light source device 16 are provided. To the light source connector 30, a water supply tank 118 is connected via an air/water supply tube 32, and a suction pump 124 is connected via a suction tube 34.

The ultrasonic processor device 12 generates an ultrasound image based on an ultrasonic detection signal output from the ultrasonic endoscope 10. The endoscopic processor device 14 generates an endoscopic image based on an image pick-up signal output from the ultrasonic endoscope 10.

To the light source device 16, the insertion section 20, the operation section 22, the universal cord 24, and the incident ends of light guides 128 (see FIG. 2) inserted through the inside of the light source connector 30 are connected. The light source device 16 supplies illumination light to the incident ends of the light guides 128. The illumination light is emitted to a treatment target area from the light guides 128 through illumination windows 90A and 90B (see FIG. 3) described below.

The monitor 18 is connected to both of the ultrasonic processor device 12 and the endoscopic processor device 14, and displays an ultrasound image generated by the ultrasonic processor device 12 and an endoscopic image generated by the endoscopic processor device 14. It is possible to selectively display only one of the ultrasound image and the endoscopic image or to display both of these images.

In the operation section 22, an air/water supply button 36 and a suction button 38 are arranged to be parallel, and a pair of angle knobs 42, an operating lever 43, a treatment tool insertion port 44, and the like are provided.

The insertion section 20 has a distal end, a proximal end, and a longitudinal axis; and has a distal end portion 50, a bending portion 52, and a soft portion 54 that are arranged in order from the distal end side toward the proximal end side. The distal end portion 50 is made of a rigid material and also referred to as a "distal end rigid portion". An ultrasonic transducer 62 is provided at the distal end portion 50, and a balloon 64 that surrounds and covers the ultrasonic transducer 62 is removably attached to the distal end portion 50.

One end of the bending portion 52 is joined to the proximal end side of the distal end portion 50, and the other end thereof is joined to the distal end side of the soft portion 54. The bending portion 52 is configured to be bendable, and is remotely operated to be bent by rotating the pair of angle knobs 42. Thus, it is possible to direct the distal end portion 50 in a desired direction.

The soft portion 54 is small in diameter, large in length, and flexible; and couples the bending portion 52 and the operation section 22.

Figure 2:
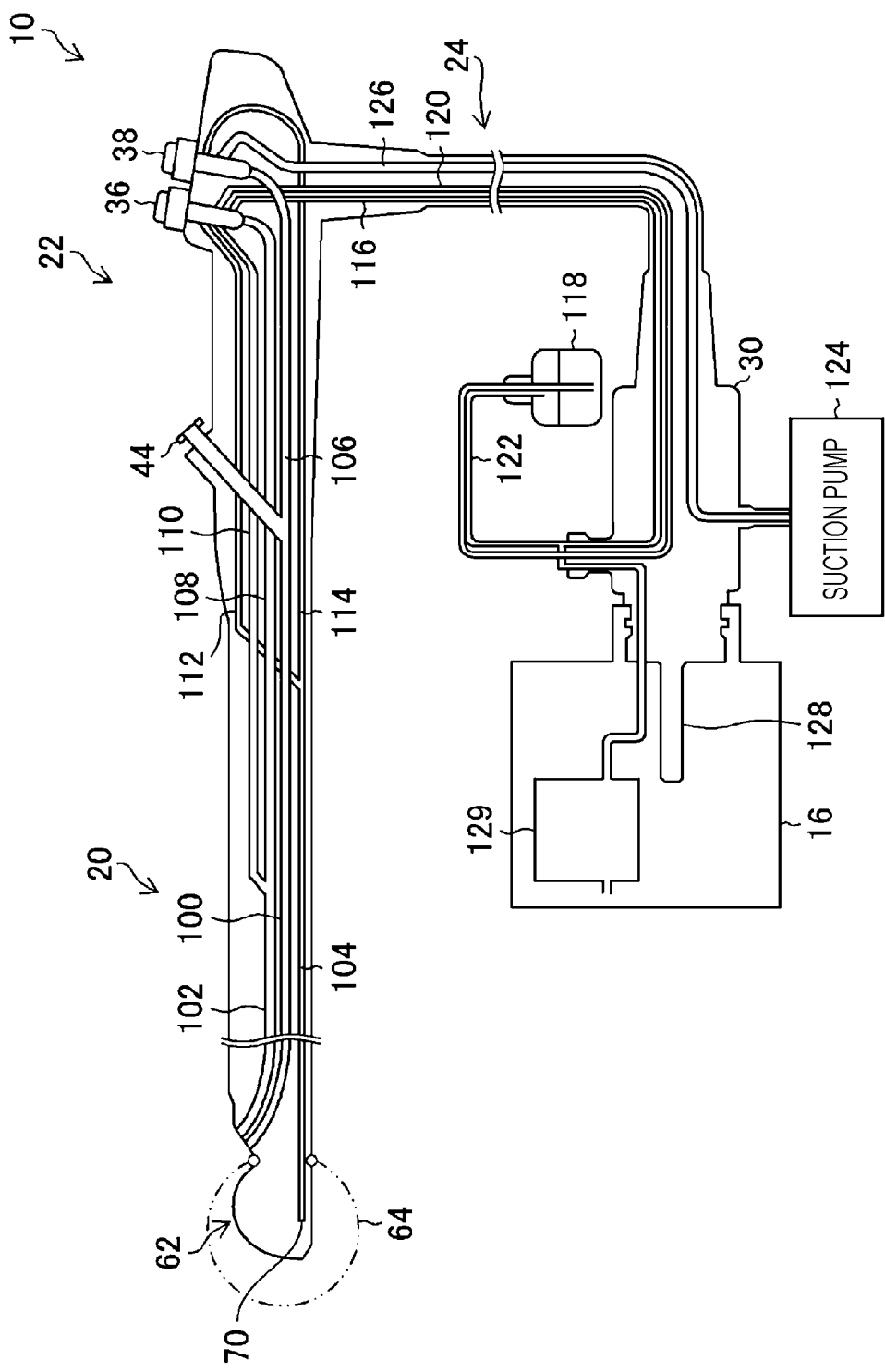
FIG. 2 is a schematic view illustrating the pipe line configuration of the ultrasonic endoscope.

FIG. 2 is a schematic view illustrating the pipe line configuration of the ultrasonic endoscope 10. As illustrated in FIG. 2, inside the insertion section 20 and the operation section 22, a treatment tool insertion channel 100, an air/water supply pipe line 102, and a balloon pipe line 104, one end which communicates with an inner space of the balloon 64, are provided.

One end side of the treatment tool insertion channel 100 is connected to an elevating case 200 (see FIG. 3) described below, and the other end side of the treatment tool insertion channel 100 is connected to the treatment tool insertion port 44 in the operation section 22. Thus, the treatment tool insertion port 44 and a treatment tool lead-out port 94 described below (see FIG. 3) communicate with each other via the treatment tool insertion channel 100. A suction pipe line 106 branches off from the treatment tool insertion channel 100, and the suction pipe line 106 is connected to the suction button 38.

One end side of the air/water supply pipe line 102 is connected to an air/water supply nozzle 92 described below (see FIG. 3), and the other end side of the air/water supply pipe line 102 branches into an air supply pipe line 108 and a water supply pipe line 110. The air supply pipe line 108 and the water supply pipe line 110 are each connected to the air/water supply button 36.

One end side the balloon pipe line 104 is connected to a supply/discharge port 70 that opens in an outer peripheral surface of the distal end portion 50 at a position inside of the balloon 64, and the other end side of the balloon pipe line 104 branches into a balloon water supply pipe line 112 and a balloon water discharge pipe line 114. The balloon water supply pipe line 112 is connected to the air/water supply button 36, and the balloon water discharge pipe line 114 is connected to the suction button 38.

To the air/water supply button 36, one end side of an air supply source pipe line 116, which communicates with an air supply pump 129, and one end side of a water supply source pipe line 120, which communicates with the water supply tank 118, are connected, in addition to the air supply pipe line 108, the water supply pipe line 110, and the balloon water supply pipe line 112. The air supply pump 129 continuously operates during an ultrasonic observation.

A branch pipe line 122 branches off from the air supply source pipe line 116, and the branch pipe line 122 is connected to an inlet of the water supply tank 118 (above the liquid level). The other end side of the water supply source pipe line 120 is inserted to the inside of the water supply tank 118 (below the liquid level). Water in the water supply tank 118 is supplied to the water supply source pipe line 120 when the internal pressure of the water supply tank 118 increases as the air supply pump 129 supplies air from via the branch pipe line 122.

A known two-step switching button is used as the air/water supply button 36. In response to an operation by an operator, the air/water supply button 36 switches among leakage of air supplied from the air supply source pipe line 116, ejection of air from the air/water supply nozzle 92, ejection of water from the air/water supply nozzle 92, and supply of water into the balloon 64. Description of a specific switching method, which is a known technology, will be omitted here.

To the suction button 38, one end side of a suction source pipe line 126 is connected, in addition to the suction pipe line 106 and the balloon water discharge pipe line 114. The suction pump 124 is connected to other end side of the suction source pipe line 126. The suction pump 124 also continuously operates during an ultrasonic observation. The suction button 38 is a two-step switching button, as with the air/water supply button 36.

In response to an operation by an operator, the suction button 38 switches among connection of the suction source pipe line 126 to the outside (atmosphere), suction of various aspirates from the treatment tool lead-out port 94 (see FIG. 3), and discharge of water in the balloon 64. Description of a specific switching method, which is a known technology, will be omitted here.

Referring back to FIG. 1, as described below in detail, the operating lever 43 of the operation section 22 is used to change the lead-out direction in which a treatment tool (not shown, the same applies hereafter) is led out from the treatment tool lead-out port 94 (see FIG. 3).

[Configuration of Distal End Portion of Insertion Section]

Figure 3:
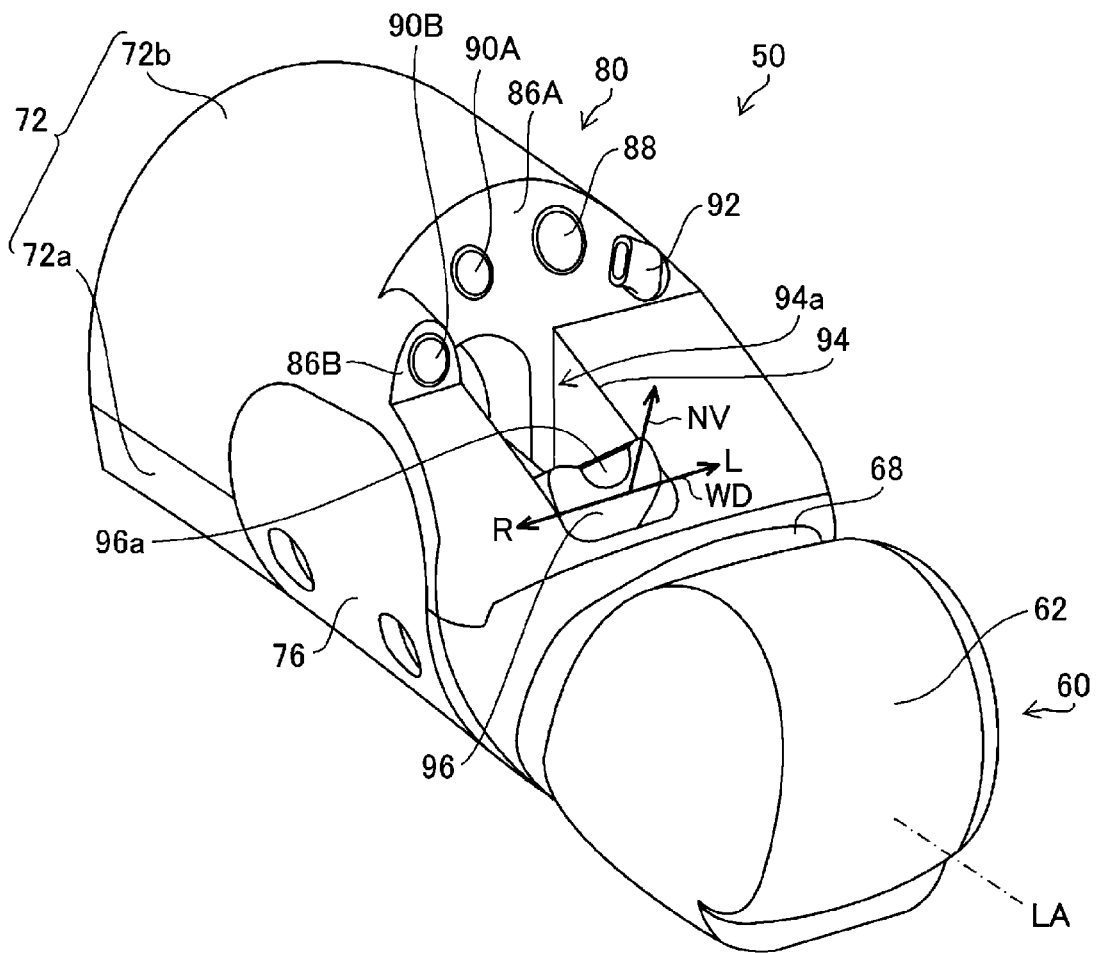
FIG. 3 is an external perspective view of a distal end portion of an insertion section.
Figure 4:
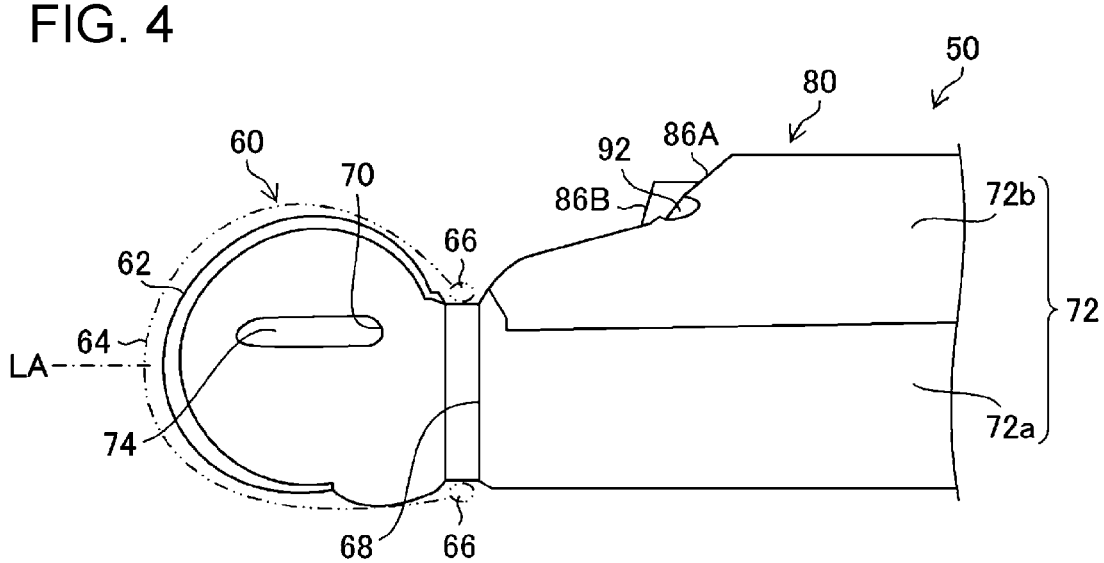
FIG. 4 is a right side view of the distal end portion of the insertion section.
Figure 5:
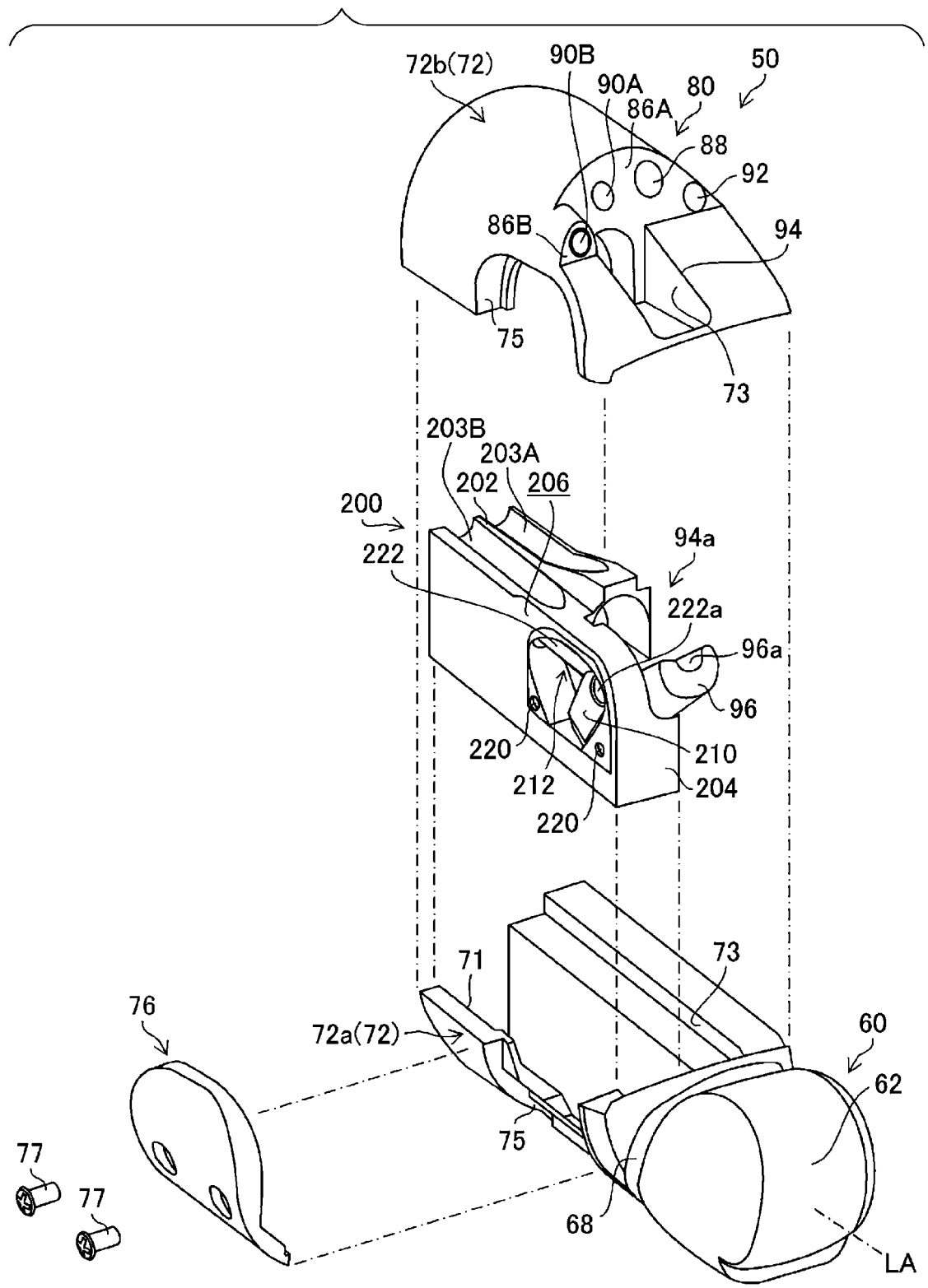
FIG. 5 is an exploded perspective view of the distal end portion of the insertion section.

FIG. 3 is an external perspective view of the distal end portion 50 of the insertion section 20. FIG. 4 is a right side view of the distal end portion 50 of the insertion section 20. FIG. 5 is an exploded perspective view of the distal end portion 50 of the insertion section 20. In FIGS. 3 and 5, illustration of the balloon 64 is omitted. In FIG. 5, illustration of the light guides 128 is omitted.

As illustrated in FIGS. 3 to 5, the distal end portion 50 includes an outer case 72 (also referred to as a "housing") corresponding to a distal end portion body in the present invention. The outer case 72 has a distal end that constitutes a distal end of the insertion section 20, a proximal end that is connected to the bending portion 52, and a longitudinal axis LA. Hereafter, the distal end side of the outer case 72 will be referred to as the "outer case distal end side", and the proximal end side of the outer case 72 will be referred to as the "outer case proximal end side".

In the outer case 72, from the outer case distal end side toward the outer case proximal end side, an ultrasonic observation portion 60 that acquires an ultrasonic detection signal, the treatment tool lead-out port 94 for a treatment tool, a first inclined surface 86A, a second inclined surface 86B, and an endoscope observation portion 80 that acquires an image pick-up signal are provided. Inside the outer case 72, an elevator housing chamber 94a and an elevator 96 that are positioned inside of the treatment tool lead-out port 94, and the elevating case 200 (also referred to as an "elevator assembly") that rotatably supports the elevator 96 and that is made of a metal are provided. Moreover, the outer case 72 includes a lever housing cover 76.

The treatment tool lead-out port 94 opens in an outer surface of the outer case 72 at a position between the ultrasonic observation portion 60 and the endoscope observation portion 80 (the first inclined surface 86A). From the treatment tool lead-out port 94, a treatment tool, which is inserted through the inside of the treatment tool insertion channel 100 of the insertion section 20, is led out. Hereafter, as illustrated in FIG. 3, a direction perpendicular to both of the longitudinal axis LA and the normal direction NV of the opening surface of the treatment tool lead-out port 94 will be referred to as the "width direction WD" of the treatment tool lead-out port 94, one side in the width direction WD will be referred to as the "L side", and the other side opposite to the one side in the width direction WD will be referred to as the "R side".

The first inclined surface 86A and the second inclined surface 86B are inclined surfaces that are inclined toward the outer case proximal end side from an orientation parallel to the width direction WD and perpendicular to longitudinal axis LA. As described below in detail, the inclination angle of the first inclined surface 86A and the inclination angle of the second inclined surface 86B are different.

The first inclined surface 86A is formed on the outer surface of the outer case 72 at a position that is on the outer case proximal end side relative to the treatment tool lead-out port 94 in the direction along the longitudinal axis LA, and is formed from a region in which the treatment tool lead-out port 94 is formed to a region on the L side thereof in the width direction WD. In the first inclined surface 86A, an observation window 88 of the endoscope observation portion 80, a first illumination window 90A, and the air/water supply nozzle 92 are provided. The first inclined surface 86A may be divided into a region in which the observation window 88 is provided, a region in which the first illumination window 90A is provided, and a region in which the air/water supply nozzle 92 is provided.

The second inclined surface 86B is formed on the outer surface of the outer case 72 at a position that is on the outer case distal end side relative to the first inclined surface 86A in the direction along the longitudinal axis LA, and is formed on the R side relative to a region in which the treatment tool lead-out port 94 is formed in the width direction WD. A second illumination window 90B is provided in the second inclined surface 86B. The second inclined surface 86B may be formed, in the direction along the longitudinal axis LA, at the same position as the first inclined surface 86A or at a position on the outer case proximal end side of the first inclined surface 86A.

The ultrasonic observation portion 60 is provided in the outer case 72 at a position on the outer case distal end side relative to the treatment tool lead-out port 94. The ultrasonic observation portion 60 includes the ultrasonic transducer 62 constituted by a plurality of ultrasonic vibrators. The ultrasonic vibrators of the ultrasonic transducer 62 are successively driven based on drive signals input from the ultrasonic processor device 12. Thus, the ultrasonic vibrators successively generate ultrasound toward a treatment target area, and receive ultrasonic echoes (echo signals) reflected by the treatment target area. The ultrasonic vibrators output ultrasonic detection signals (electric signals), which correspond to the received ultrasonic echoes, to the ultrasonic processor device 12 via a signal cable (not shown) inserted through the inside of the insertion section 20, the universal cord 24, and the like. As a result, an ultrasound image is generated by the ultrasonic processor device 12.

The balloon 64 is attached to the outer case 72 at a position on the outer case distal end side relative to the treatment tool lead-out port 94, has a bag-like shape that surrounds and covers the ultrasonic transducer 62, and prevents attenuation of ultrasound and an ultrasonic echo. The balloon 64 is made of an elastic material such as latex rubber, and an elastic locking ring 66 is provided at an open end on the outer case proximal end side thereof. In a part of the outer case 72 between the ultrasonic observation portion 60 and the treatment tool lead-out port 94, a locking groove 68 is provided around the entire circumference of the outer case 72 in circumferential direction. The balloon 64 is removably attached the outer case 72 by fitting the locking ring 66 to the locking groove 68.

The endoscope observation portion 80 has the observation window 88 provided in the first inclined surface 86A. Although illustrations are omitted, in a region in the outer case 72 and behind the observation window 88, an observation optical system (an objective lens and the like) that constitutes the endoscope observation portion 80, an imaging device such as a CCD (Charge Coupled Device) or a CMOS (Complementary Metal Oxide Semiconductor)

device, and the like are disposed. The imaging device picks up an observation image captured through the observation window 88. The imaging device outputs an image signal of the observation image to the endoscopic processor device 14 through a signal cable (not shown) inserted through the inside of the insertion section 20, the universal cord 24, and the like. As a result, an endoscopic image is generated by the endoscopic processor device 14.

As described below in detail, the first illumination window 90A and the second illumination window 90B each emit illumination light in the forward direction thereof. In a region in the outer case 72 and behind the illumination windows 90A and 90B, the emission ends of the aforementioned light guides 128 are disposed. Accordingly, by coupling the light source connector 30 to the light source device 16 as illustrated in the aforementioned FIG. 2, illumination light emitted from the light source device 16 is guided to the illumination windows 90A and 90B via the light guides 128, and the illumination light is emitted from the illumination windows 90A and 90B.

The air/water supply nozzle 92 is disposed on the first inclined surface 86A at a position in the vicinity of the observation window 88. The air/water supply nozzle 92 is connected to one end side of the air/water supply pipe line 102 illustrated in the aforementioned FIG. 2, and ejects a fluid such as water or air toward the observation window 88 in order to wash away foreign substances and the like that adhere to the surface of the observation window 88.

The outer case 72 houses the ultrasonic observation portion 60 and the endoscope observation portion 80, which are described above, and the elevator 96 and the elevating case 200, which are described below. A part in the outer case 72 on the outer case proximal end side relative to the ultrasonic observation portion 60 is divided into two in the up-down direction in the figure along a plane parallel to both of the longitudinal axis LA and the width direction WD. Therefore, the outer case 72 is constituted by an outer case body 72a, which is positioned on the lower side in the figure, and an outer case cover 72b, which is positioned on the upper side in the figure.

The outer case body 72a houses the ultrasonic observation portion 60 and has the locking groove 68 in a distal end part on the outer case distal end side relative to the treatment tool lead-out port 94. The outer case body 72a has an opening portion 71 that is provided in a part on the outer case proximal end side relative to the locking groove 68 and that is covered by the outer case cover 72b (see FIG. 5). The outer case body 72a houses a part of each of the elevator 96 and the elevating case 200 in the opening portion 71.

In a side surface of the distal end part of the outer case body 72a on the L side, a groove portion 74 (see FIG. 4), which is formed along the longitudinal axis LA, and the supply/discharge port 70, which opens at an end portion of the groove portion 74 on the outer case proximal end side, are formed. Thus, it is possible to supply water into the balloon 64 through the supply/discharge port 70 or to discharge water in the balloon 64 through the supply/discharge port 70.

The outer case cover 72b is removably attached to the opening portion 71 of the outer case body 72a. In the outer case cover 72b, from the outer case distal end side toward the outer case proximal end side, the aforementioned treatment tool lead-out port 94, the first inclined surface 86A, and the second inclined surface 86B are formed. The outer case cover 72b covers the endoscope observation portion 80 and two light guides 128 that guide illumination light to the illumination windows 90A and 90B.

When the outer case cover 72b is attached to the opening portion 71 of the outer case body 72a, the elevator housing chamber 94a, which is a space for housing the elevator 96, is formed inside the treatment tool lead-out port 94. A partition wall 73 (see FIG. 5), which constitutes a side surface of the elevator housing chamber 94a on the L side, is formed astride both of the outer case body 72a and the outer case cover 72b.

In side surfaces of the outer case body 72a and the outer case cover 72b on the R side at a position facing a lever housing chamber 212 (see FIG. 5) of the elevating case 200 described below, a fitting hole 75 (see FIG. 5), to which the lever housing cover 76 is fitted, is formed astride the outer case body 72a and the outer case cover 72b.

The elevator housing chamber 94a communicates with the treatment tool insertion port 44 through the aforementioned treatment tool insertion channel 100 (see FIG. 2) and the like. Therefore, a treatment tool inserted into the treatment tool insertion port 44 is led into the lumen 154 (see FIG. 12) from the treatment tool lead-out port 94 via the treatment tool insertion channel 100, the elevator housing chamber 94a, and the like.

Figure 6:
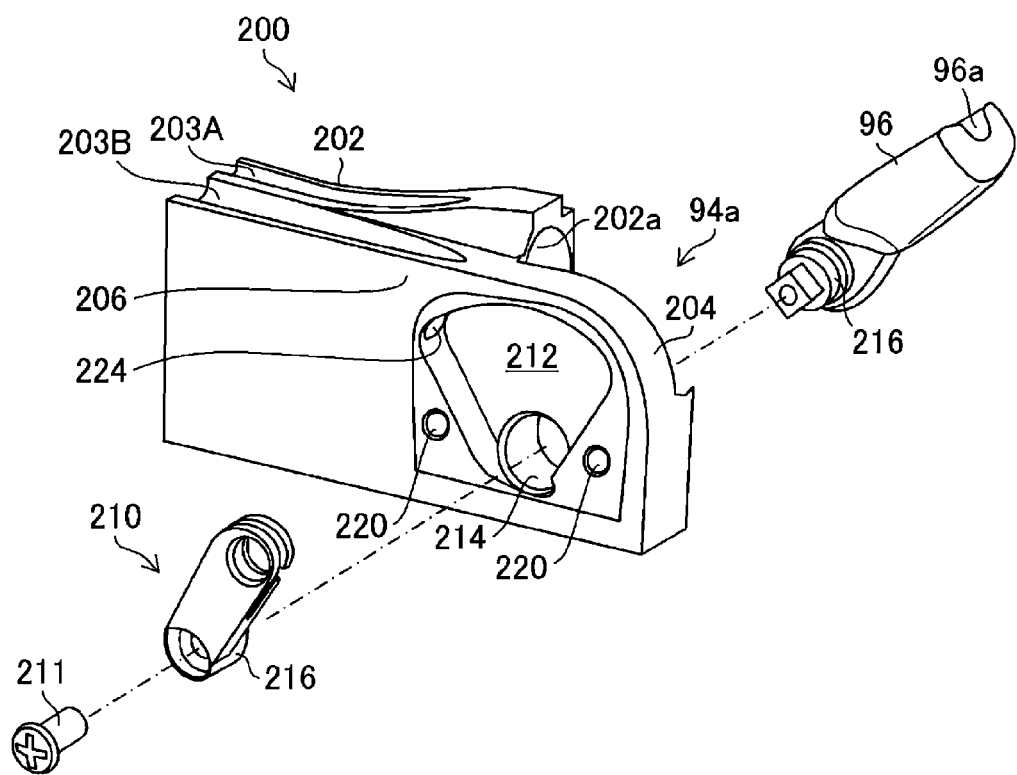
FIG. 6 is a perspective view of an elevating case.

The elevator 96 is rotatably supported by the elevating case 200 in the elevator housing chamber 94a via a rotation shaft 216 (see FIG. 6). The elevator 96 has an arc-shaped guide surface 96a that guides a treatment tool, which has been led into the elevator housing chamber 94a, toward the treatment tool lead-out port 94. Thus, the elevator 96 changes the direction of the treatment tool, which has been guided into the elevator housing chamber 94a from the treatment tool insertion channel 100, and leads out the treatment tool from the treatment tool lead-out port 94. As described below in detail, the elevator 96 rotates in the elevator housing chamber 94a around the rotation shaft 216 in response to an operation on the operating lever 43, and thereby changes the lead-out direction in which the treatment tool is led out from the treatment tool lead-out port 94 into the lumen 154 (see FIG. 12). Accordingly, the elevator 96 controls the lead-out direction in which the treatment tool is led out from the treatment tool lead-out port 94.

The lever housing cover 76 is fitted to the fitting hole 75 in the outer surface of the outer case 72. In a state of being fitted to the fitting hole 75, the lever housing cover 76 is removably attached to the elevating case 200 by using bolts 77 that extend through the lever housing cover 76 (see FIG. 5).

[Configuration of Elevating Case]

Figure 7:
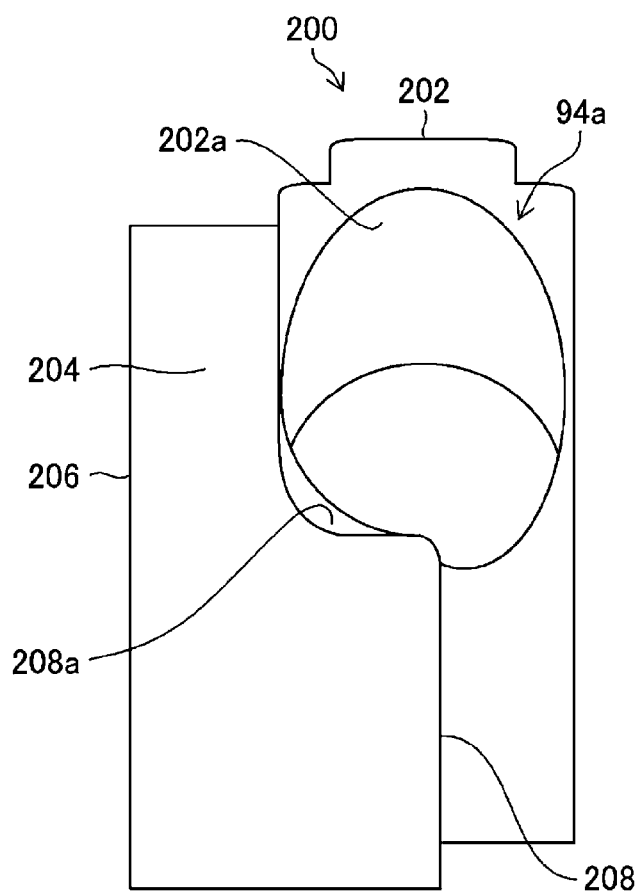
FIG. 7 is a front view of the elevating case when the elevating case is seen from the outer case distal end side.

FIG. 6 is a perspective view of the elevating case 200, and FIG. 7 is a front view of the elevating case 200 when the elevating case 200 is seen from the outer case distal end side. As illustrated in FIGS. 6 and 7 and the aforementioned FIG. 5, the elevating case 200 corresponds to an elevator support member in the present invention, and is made of, for example, a corrosion-resistant metal material. The elevating case 200 has a base 202 and a partition wall 204 extending from the base 202 toward the outer case distal end side.

A distal end surface on the outer case distal end side of the base 202 constitutes a side surface of the elevator housing chamber 94a on the outer case proximal end side. In the base 202, a through hole 202a that is parallel to the longitudinal axis LA and that communicates with the elevator housing chamber 94a and the treatment tool insertion channel 100 is formed. Thus, the treatment tool insertion channel 100 and the elevator housing chamber 94a communicate with each other via the through hole 202a.

Two light guide holding grooves 203A and 203B are formed in an upper surface (a surface on the treatment tool lead-out side) of the outer wall of the base 202. Here, the two light guides 128, respectively corresponding to the illumination windows 90A and 90B, are disposed along the upper surface of the base 202, because the illumination windows 90A and 90B are disposed on the upper side of the elevating case 200 (on a side in a direction perpendicular to both of the longitudinal axis LA and the width direction WD). Thus, with each of the light guide holding grooves 203A and 203B, one of emission end of each of the light guides 128 is held at a position facing the first illumination window 90A, and the other emission end of each of the light guides 128 is held at a position facing the second illumination window 90B.

The partition wall 204 is provided between the elevator 96 (the elevator housing chamber 94a) and an elevator elevating lever 210 (the lever housing chamber 212) described below. The partition wall 204 has a side wall 206, which is a side surface on the R side thereof, and a counter wall 208, which is a side surface on the L side thereof and faces the elevator 96.

In the side wall 206, the lever housing chamber 212, which houses the elevator elevating lever 210, is formed. In a bottom surface of the lever housing chamber 212 on the elevator 96 side, a holding hole 214 (see FIG. 6), which extends through the partition wall 204 in the width direction WD (the axial direction of the rotation shaft 216), is formed. The holding hole 214 connects the lever housing chamber 212 and the elevator housing chamber 94a to each other. The holding hole 214 rotatably supports the rotation shaft 216. The lever housing chamber 212 has a fan-like shape around the rotation shaft 216, because the elevator elevating lever 210 in the lever housing chamber 212 rotates (swings) around the rotation shaft 216.

A wire insertion hole 224 (see FIG. 6), through which an operating wire 222 is inserted, is formed in a side wall of the lever housing chamber 212 on the outer case proximal end side.

Bolt holes 220, into which the aforementioned bolts 77 are screwed, are formed in a region of the side wall 206 that is a peripheral region of the lever housing chamber 212 and that is covered by the lever housing cover 76. The number of the bolts 77 and the bolt holes 220 is not particularly limited.

The counter wall 208 constitutes a side surface of the elevator housing chamber 94a on the R side. The holding hole 214 opens in the counter wall 208. A cutout portion 208a (see FIG. 7), into which a part of the elevator 96 enters, is formed in the counter wall 208.

The elevator elevating lever 210 rotates the elevator 96 around the rotation shaft 216 in response to an operation on the operating lever 43. One part of the rotation shaft 216 having a two-part structure is provided at one end portion of the elevator elevating lever 210, and the operating wire 222 is coupled to the other end portion of the elevator elevating lever 210.

One part of the rotation shaft 216 having a two-part structure is provided at one end portion of the elevator elevating lever 210 as described above, and the other part of the rotation shaft 216 is provided at one end portion of the elevator 96. The elevator elevating lever 210 and the elevator 96 are coupled to each other via the rotation shaft 216 having a two-part structure. For example, in the present embodiment, one part and the other part of the rotation shaft 216 having a two-part structure are coupled to each other by using a bolt 211 extending through one end side of the elevator elevating lever 210, and thereby the elevator elevating lever 210 and the elevator 96 are coupled to each other via the rotation shaft 216 (see FIG. 6). Thus, the elevator elevating lever 210 rotates (swings) around the rotation shaft 216 together with the elevator 96.

The operating wire 222 has, on one end side thereof, a distal end side coupling portion 222a (see FIG. 5) that is coupled to the elevator elevating lever 210 in the lever housing chamber 212. The other end side of the operating wire 222 extends from the wire insertion hole 224 of the lever housing chamber 212 through the insertion section 20 and is coupled to an elevator operating mechanism 226 (see FIG. 8) in the operation section 22.

Figure 8:
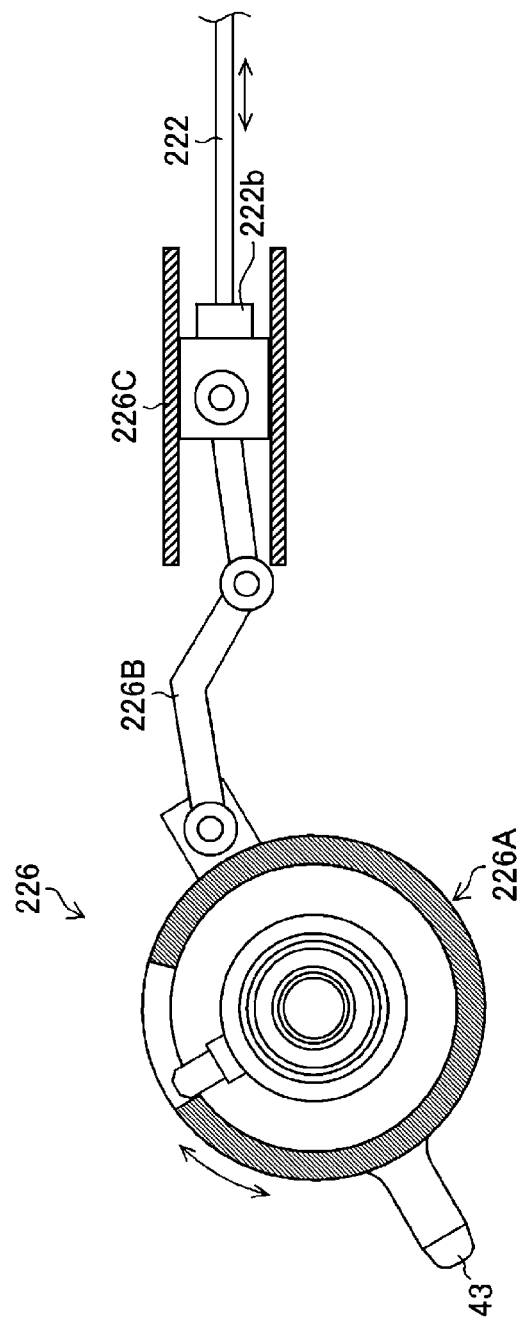
FIG. 8 is a schematic view of an example of an elevator operating mechanism.

FIG. 8 is a schematic view of an example of the elevator operating mechanism 226. As illustrated in FIG. 8, the operating wire 222 has, on the proximal end side thereof, a proximal end side coupling portion 222b that is coupled to the elevator operating mechanism 226. The elevator operating mechanism 226 includes the operating lever 43, a rotary drum 226A to which the operating lever 43 is coupled and that is rotatable in a predetermined angular range, a crank member 226B that is coupled to the rotary drum 226A, and a slider 226C that is coupled to the crank member 226B. The proximal end side coupling portion 222b is coupled to the slider 226C.

When the operating lever 43 is operated to rotate the rotary drum 226A, the elevator elevating lever 210 swings as the operating wire 222 is pushed and pulled via the crank member 226B and the slider 226C, and the elevator 96 rotates (swings) around the rotation shaft 216 in response to the swing of the elevator elevating lever 210.

Figure 9:
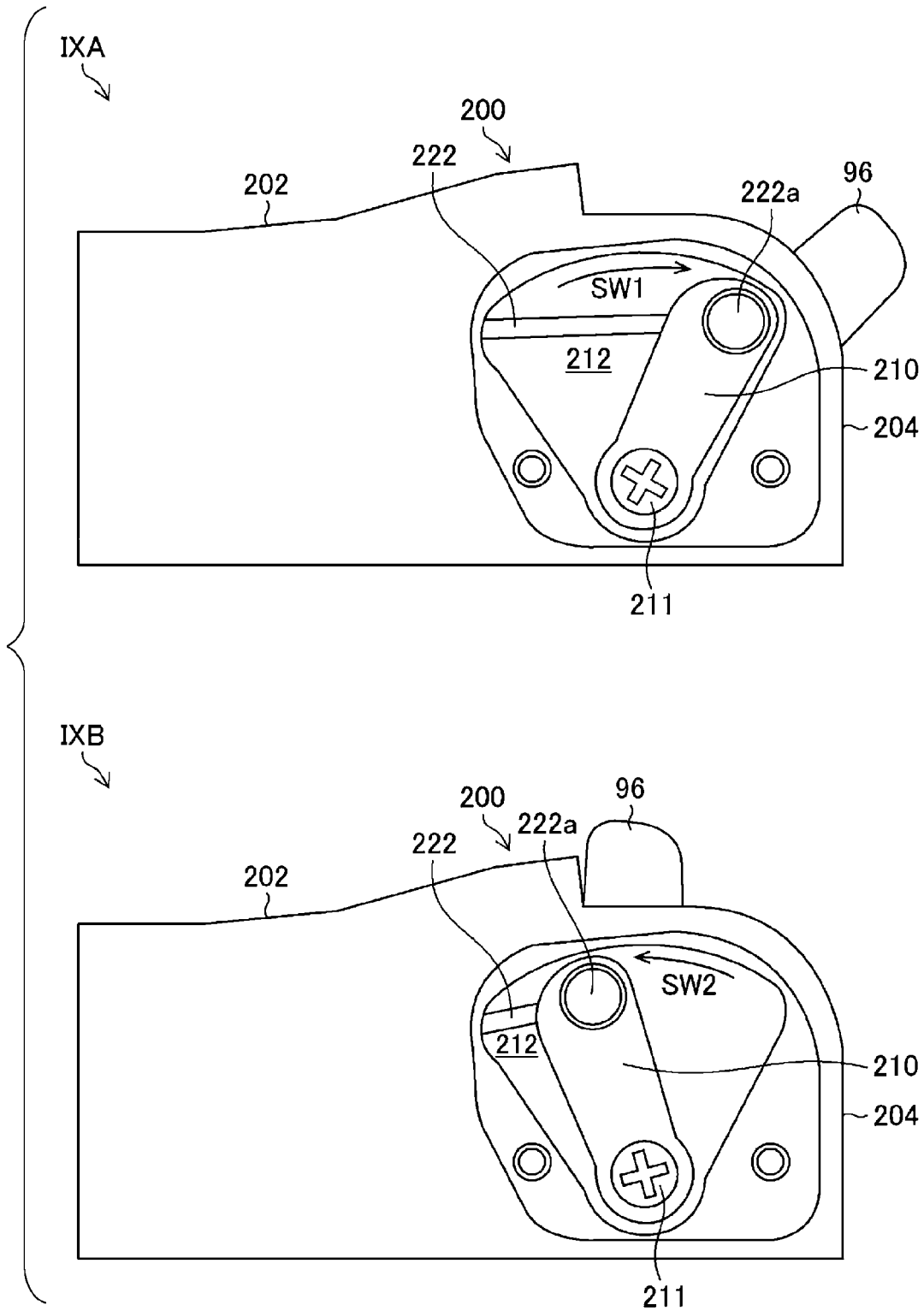
FIG. 9 illustrates rotation of an elevator in response to an operation on an operating lever.

FIG. 9 illustrates rotation of the elevator 96 in response to an operation on the operating lever 43. As shown in a part IXA in FIG. 9, when the operating lever 43 is operated to rotate the rotary drum 226A in one direction, the operating wire 222 is pushed, and thereby the elevator elevating lever 210 rotates around the rotation shaft 216 in a direction SW1. Thus, the elevator 96 rotates to a lowered position due to the rotation.

As shown in a part IXB in FIG. 9, when the operating lever 43 is operated to rotate the rotary drum 226A in the opposite direction, the operating wire 222 is pulled, and thereby the elevator elevating lever 210 rotates around the rotation shaft 216 in a direction SW2 opposite to the direction SW1. Thus, the elevator 96 rotates to an elevated position due to the rotation. Thus, it is possible to cause the elevator 96 to be displaced (elevated or lowered) by operating the operating lever 43 to rotate the rotation shaft 216 via the operating wire 222, the elevator elevating lever 210, and the like.

[First Illumination Window, Second Illumination Window, and Observation Window]

Figure 10:
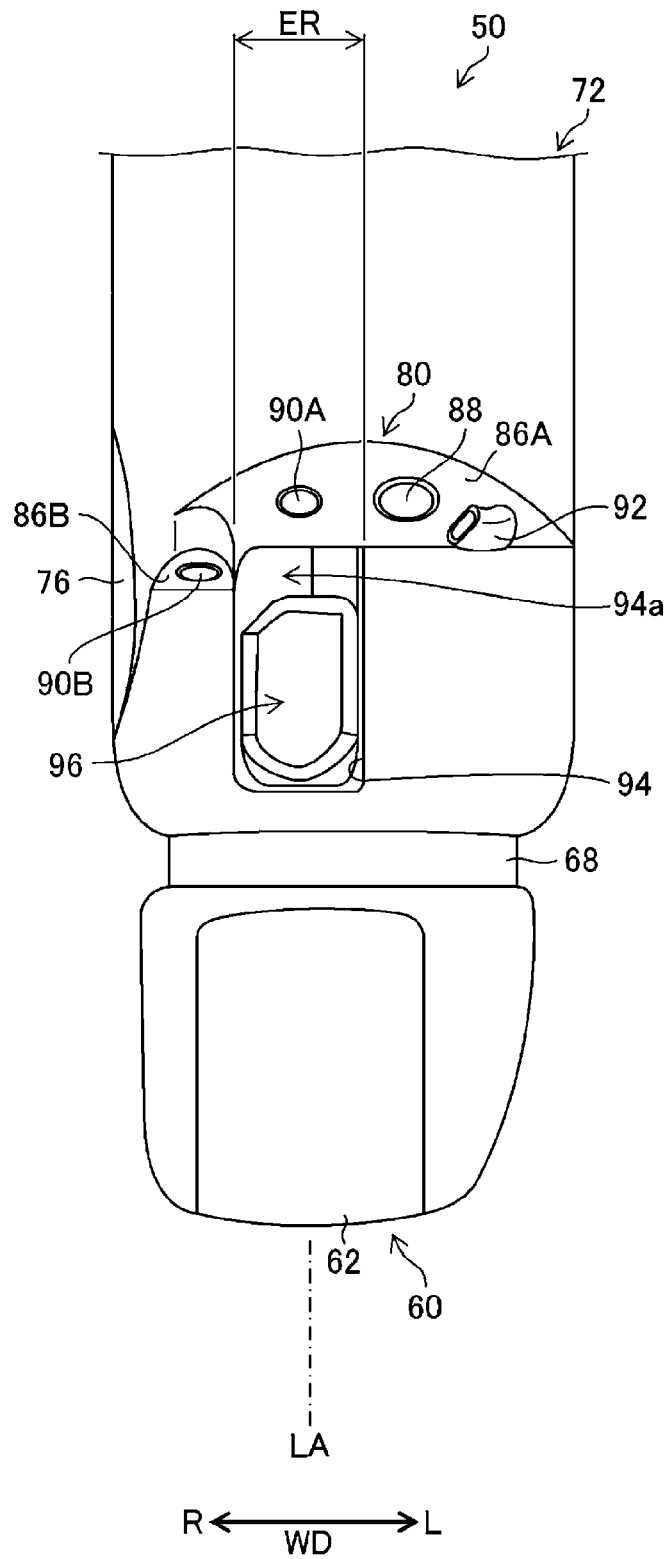
FIG. 10 is a top view of the outer case.

FIG. 10 is a top view of the outer case 72. As illustrated in FIG. 10, the first illumination window 90A is formed in a proximal end side region ER in the aforementioned first inclined surface 86A. The proximal end side region ER is a region in the outer surface of the outer case 72 that is at a position shifted from the treatment tool lead-out port 94 toward the outer case proximal end side.

To be more specific, the proximal end side region ER is a region in the outer case 72 that is positioned on the outer case proximal end side relative to the treatment tool lead-out port 94 in the direction along the longitudinal axis LA and that is in an area where the treatment tool lead-out port 94 is formed in the width direction WD. Thus, it is possible to illuminate a treatment tool led out from the treatment tool lead-out port 94 and a treatment target area thereof with illumination light emitted from the first illumination window 90A.

Moreover, when an end portion of the elevator 96 opposite to one end portion at which the rotation shaft 216 is provided is defined as the other end portion of the elevator 96, the first illumination window 90A is provided at a position in the outer case 72 (the proximal end side region ER) on the outer case proximal end side relative to the other end portion of the elevator 96, at least when the elevator 96 is in the lowered position. In other words, the other end portion of the elevator 96 is positioned on the outer case distal end side relative to the first illumination window 90A, at least when the elevator 96 is in the lowered position. Thus, it is possible to illuminate a treatment tool led out from the treatment tool lead-out port 94 and a treatment target area thereof with illumination light emitted from the first illumination window 90A.

More preferably, the first illumination window 90A is provided on the outer case proximal end side relative to the other end portion of the elevator 96 even when the elevator 96 is in the elevated position (that is, irrespective of the rotation position of the elevator 96). Thus, even when the elevator 96 is rotated (fully elevated) to the elevated position, it is possible to illuminate a treatment tool led out from the treatment tool lead-out port 94 and a treatment target area thereof with illumination light emitted from the first illumination window 90A.

As described above, the observation window 88 is provided in the first inclined surface 86A. The observation window 88 is provided in the outer case 72 at a position on the outer case proximal end side relative to the treatment tool lead-out port 94 in the direction along the longitudinal axis LA, as with the first illumination window 90A. Thus, through the observation window 88, it is possible to observe a treatment tool led out from the treatment tool lead-out port 94 and a treatment target area thereof.

The observation window 88 is provided in the first inclined surface 86A at a position on the L side with respect to the proximal end side region ER. By thus disposing the observation window 88 and the first illumination window 90A in the same first inclined surface 86A, that is, at substantially the same position in the direction along the longitudinal axis LA, it is possible to illuminate an observation range 150B (see FIG. 11) of the observation window 88 with illumination light emitted from the first illumination window 90A.

The second illumination window 90B is provided in the second inclined surface 86B of the aforementioned outer case 72. As described below in detail, the second illumination window 90B differs from the first illumination window 90A in the emission direction of illumination light.

The air/water supply nozzle 92 is provided on the first inclined surface 86A at a position on the L side relative to the observation window 88. As described above, the air/water supply nozzle 92 cleans the observation window 88 by ejecting a fluid such as water or air to the observation window 88. In order that both of the illumination windows 90A and 90B are included in the ejection range of a fluid ejected from the air/water supply nozzle 92 at this time, the position where the first illumination window 90A is formed in the proximal end side region ER and the position where the second illumination window 90B is formed in the second inclined surface 86B are each adjusted. Thus, it is possible to cool the illumination windows 90A and 90B and the light guide distal end portions 141A and 141B (see FIG. 13) of the light guides 128 by using a fluid ejected from the air/water supply nozzle 92.

Figure 11:
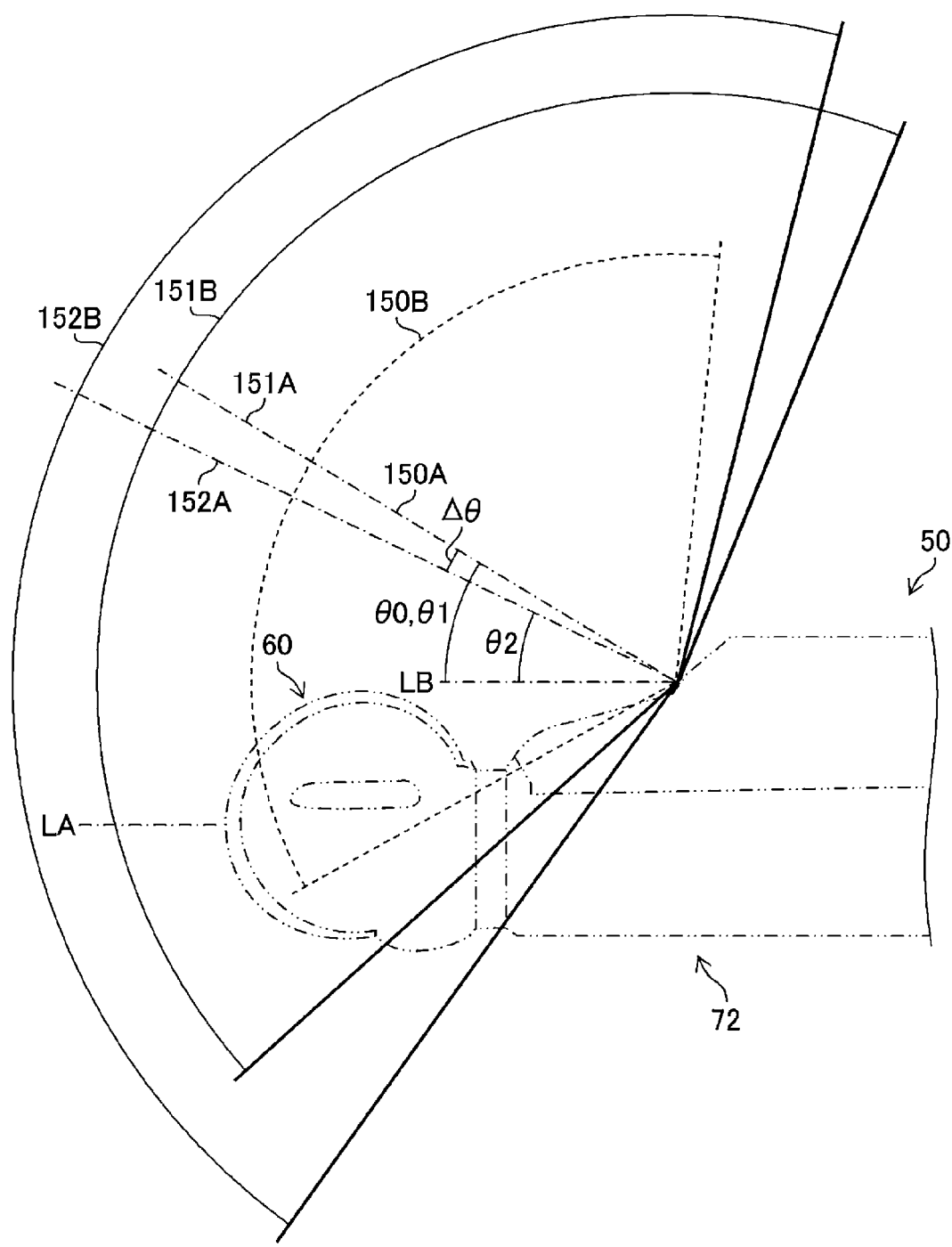
FIG. 11 illustrates an observation axis and an observation range of an observation window, a first illumination axis and a first illumination range of a first illumination window, and a second illumination axis and a second illumination range of a second illumination window.

FIG. 11 illustrates an observation axis 150A and an observation range 150B of the observation window 88, a first illumination axis 151A and a first illumination range 151B of the first illumination window 90A, and a second illumination axis 152A and a second illumination range 152B of the second illumination window 90B. In FIG. 11 (also in FIG. 12 described below), in order to prevent complexity of the figure, the axes and the areas are illustrated on the assumption that the observation window 88 and the illumination windows 90A and 90B are at the same position.

As illustrated in FIG. 11, the observation axis 150A is an axis extending from the observation window 88 in the normal direction thereof, the first illumination axis 151A is an axis extending from the first illumination window 90A in the normal direction thereof, and the second illumination axis 152A is an axis extending from the second illumination window 90B in the normal direction thereof. The observation axis 150A, the first illumination axis 151A, and the second illumination axis 152A are each an inclined axis that is inclined toward the outer case distal end side from an orientation perpendicular to both of the width direction WD and the longitudinal axis LA. The observation axis 150A and the first illumination axis 151A are parallel to a normal line of the first inclined surface 86A, and the second illumination axis 152A is parallel to a normal line of the second inclined surface 86B.

An observation axis angle $\theta 0$ is the inclination angle of the observation axis 150A with respect to a reference axis LB parallel to the longitudinal axis LA as seen in the width direction WD (the side in the direction perpendicular to the plane of the figure). A first illumination axis angle $\theta 1$ is the inclination angle of the first illumination axis 151A with respect to the reference axis LB as seen in the width direction WD. A second illumination axis angle $\theta 2$ is the inclination angle of the second illumination axis 152A with respect to the reference axis LB as seen in the width direction WD. The reference axis LB is an axis that intersects the observation axis 150A for the observation axis angle $\theta 0$, is an axis that intersects the first illumination axis 151A for the first illumination axis angle $\theta 1$, and is an axis that intersects the second illumination axis 152A for the second illumination axis angle $\theta 2$.

The observation axis angle $\theta 0$ and the observation range 150B are each set at a value such that, as seen in the width direction WD, it is possible to observe through the observation window 88 an angular range from one to the other of the outer case distal end side of the outer case 72 [the insertion direction side (forward-direction side) of the insertion section 20] and a treatment tool led out from the treatment tool lead-out port 94 and a treatment target area thereof. Preferably, the observation axis angle $\theta 0$ and the observation range 150B have values such that it is possible to observe a treatment tool led out from the treatment tool lead-out port 94 and a treatment target area thereof in a state in which the elevator 96 is rotated to the elevated position.

The first illumination axis 151A and the observation axis 150A are parallel (including "substantially parallel"), because the first illumination axis angle $\theta 1$ and the observation axis angle $\theta 0$ are equal (including "substantially equal"). The first illumination range 151B includes the observation range 150B at least as seen in the width direction WD. Thus, the first illumination window 90A can illuminate the aforementioned angular range (the observation range 150B) with illumination light.

The second illumination axis 152A is inclined further toward the outer case distal end side than the first illumination axis 151A, because the second illumination axis angle $\theta 2$ is smaller than the first illumination axis angle $\theta 1$.

In other words, the inclination angle of the second inclined surface 86B is closer to the right angle with respect to the reference axis LB than the inclination angle of the first inclined surface 86A.

When the difference between the first illumination axis angle θ1 and the second illumination axis angle θ2 is denoted by Δθ, the second illumination range 152B is inclined toward the outer case distal end side by the difference Δθ with respect to the first illumination range 151B. Accordingly, the second illumination range 152B partially overlaps the first illumination range 151B.

In this case, the second illumination axis angle θ2 (the difference Δθ) is set at a value such that the observation range 150B is included in the second illumination range 152B at least as seen in the width direction WD. Therefore, the second illumination window 90B can also illuminate the aforementioned angular range (the observation range 150B) with illumination light.

Figure 12:
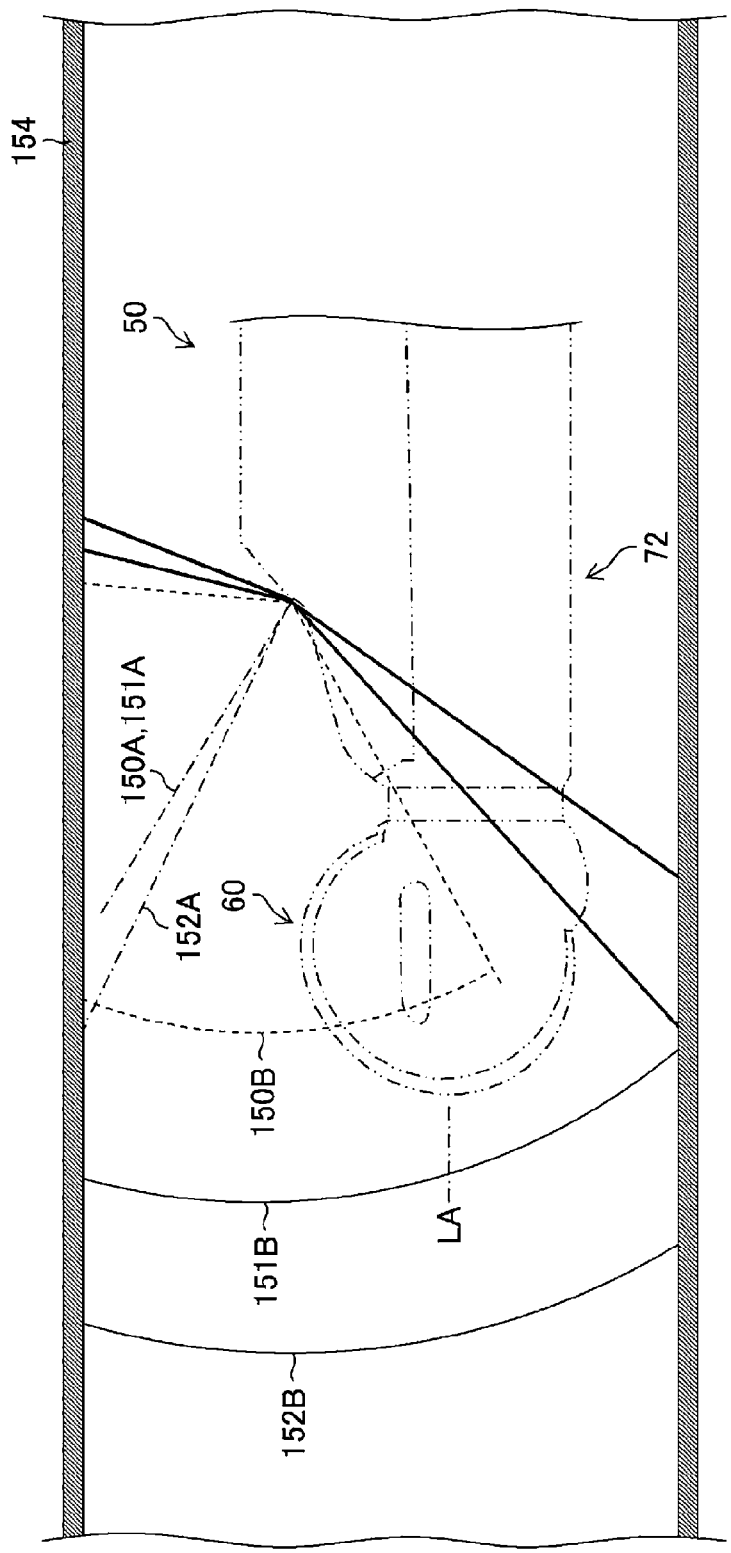
FIG. 12 is a side view of the distal end portion of the insertion section that is inserted into a lumen.

FIG. 12 is a side view of the distal end portion 50 of the insertion section 20 that is inserted into the lumen 154. As illustrated in FIG. 12 and the aforementioned FIG. 11, the second illumination window 90B (the second illumination axis 152A and the second illumination range 152B) is inclined toward the outer case distal end side by the difference Δθ relative to the first illumination window 90A (the first illumination axis 151A and the first illumination range 151B), and thereby it is possible to increase the amount of illumination light with which the second illumination window 90B illuminates the insertion direction side of the insertion section 20. As a result, for example, when the insertion section 20 is inserted into a narrow lumen 154, the visibility of an inner wall of the lumen 154 on the insertion direction side of the insertion section 20 (forward visibility) is improved.

Moreover, the second illumination window 90B is inclined toward the outer case distal end side by the difference Δθ relative to the first illumination window 90A, and thereby, when illuminating an inner wall of a narrow lumen 154 such as the duodenum, it is possible to reduce the amount of illumination light emitted from the second illumination window 90B to the inner wall compared with the amount of illumination light emitted from the first illumination window 90A to the inner wall. Thus, it is possible to reduce the amount of illumination light emitted to the inner wall of the lumen 154, compared with a case where the second illumination axis angle θ2 and the first illumination axis angle θ1 are the same. As a result, occurrence of halation of an endoscopic image, which may occur if an excessive amount of illumination light is emitted to the inner wall of the lumen 154, is prevented. As necessary, it may be configured that illumination through only the second illumination window 90B can be selectively performed.

Because the first illumination window 90A is disposed in the aforementioned proximal end side region ER, the first illumination window 90A can illuminate a treatment tool led out from the treatment tool lead-out port 94 and a treatment target area thereof constantly from one side (the proximal end side region ER side). Thus, the treatment target area is prevented from being shadowed by the elevator 96, the treatment tool, or the like as seen from the first illumination window 90A. Moreover, because the way in which a treatment tool is illuminated with illumination light does not change depending on displacement of the treatment tool due to rotation of the elevator 96, it is possible to prevent the visibility of an endoscopic image from decreasing and to prevent a treatment tool led out from the treatment tool lead-out port 94 and a treatment target area thereof from deviating from the first illumination range 151B. As a result, it is possible to reliably illuminate a treatment tool led out from the treatment tool lead-out port 94 and a treatment target area thereof with illumination light emitted from the first illumination window 90A, and thus it is possible to improve the visibility of the treatment tool and the treatment target area.

Moreover, the first illumination window 90A (the first illumination axis 151A and the first illumination range 151B) is inclined toward the outer case proximal end side by the difference Δθ relative to the second illumination window 90B (the second illumination axis 152A and the second illumination range 152B), and thereby it is possible to increase the amount of illumination light with which the first illumination window 90A illuminates a treatment tool led out from the treatment tool lead-out port 94 and a treatment target area thereof. As a result, it is possible to improve the visibility of the treatment tool and the treatment target area, because it is possible to reliably illuminate the treatment tool and the treatment target area with illumination light.

Thus, by using such a combination of the first illumination window 90A and the second illumination window 90B, it is possible to improve the forward visibility of the insertion section 20 and the visibility of the treatment tool and the treatment target area.

[Modifications of First Illumination Window, Second Illumination Window, and Observation Window]

In the present embodiment, the entirety of the first illumination window 90A is within the proximal end side region ER in the width direction WD. However, a part of the first illumination window 90A may protrude from the proximal end side region ER toward the L side or the R side. However, preferably, the entirety of the first illumination window 90A is within the proximal end side region ER in the width direction WD, in order that the first illumination window 90A can illuminate a treatment tool and a treatment target area thereof with illumination light irrespective of the rotation position of the elevator 96.

In the present embodiment, the first illumination axis angle θ1 of the first illumination axis 151A of the first illumination window 90A is less than 90°. However, the first illumination axis angle θ1 may be 90° (including "substantially 90°"), depending on the size of the first illumination range 151B of the first illumination window 90A. That is, the proximal end side region ER (the first inclined surface 86A) may be a surface parallel to the longitudinal axis LA.

In the present embodiment, the observation window 88 is formed at a position in the first inclined surface 86A and on the L side of the proximal end side region ER. However, the position where the observation window 88 is formed is not particularly limited. However, in order to constantly observe a treatment tool led out from the treatment tool lead-out port 94 and a treatment target area thereof, preferably, the observation window 88 is provided in the outer case 72 at a position on the outer case proximal end side relative to the treatment tool lead-out port 94.

In the present embodiment, the second illumination window 90B is formed in the second inclined surface 86B. However, the position where the second illumination window 90B is formed is not particularly limited. In the above embodiment, the second illumination axis angle θ2 is smaller than the first illumination axis angle θ1. However, the second illumination axis angle θ2 may be larger than the first illumination axis angle θ1, or these angles may be the same. Moreover, in the embodiment, the second illumination window 90B is provided in the outer case 72 at a position on the outer case distal end side relative to the proximal end side region ER. However, the second illumination window 90B may be provided at a position on the outer case proximal end side relative to the treatment tool lead-out port 94. Furthermore, the second illumination window 90B may be omitted, provided that the first illumination window 90A alone can reliably provide the aforementioned forward visibility and the visibility of a treatment tool and a treatment target area.

In the present embodiment, the observation axis 150A and the first illumination axis 151A are parallel. However, these axes may not be parallel. For example, the observation axis angle θ0 may be an angle between the first illumination axis angle θ1 and the second illumination axis angle θ2.

[Heat Dissipation of Light Guide Distal End Portion]

Figure 13:
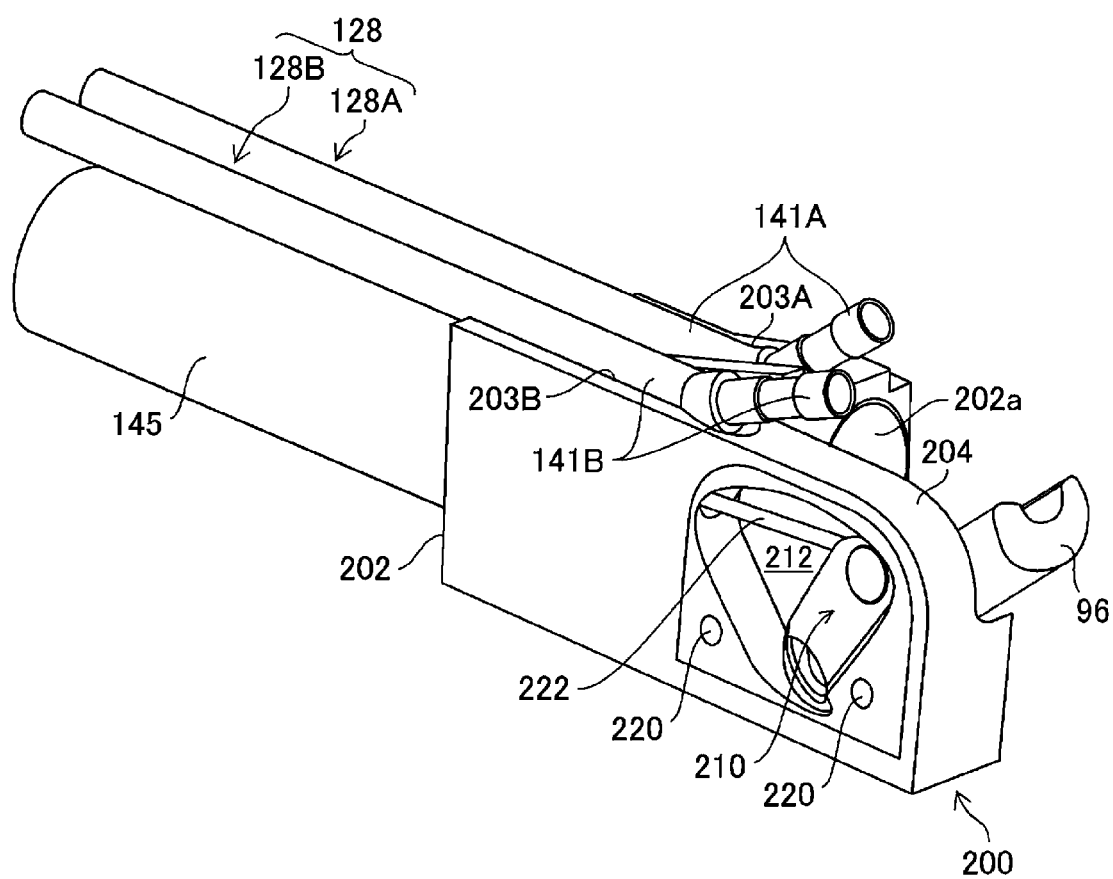
FIG. 13 is a perspective view of the elevating case and light guides that are held by the elevating case.

FIG. 13 is a perspective view of the elevating case 200 and the light guides 128 (a first light guide 128A and a second light guide 128B) held by the elevating case 200.

As illustrated in FIG. 13, the light guides 128 include the first light guide 128A, which emits illumination light through the first illumination window 90A, and the second light guide 128B, which emits illumination light through the second illumination window 90B. The first illumination window 90A and the second illumination window 90B constitute an illumination window in the present invention.

The first light guide 128A has the light guide distal end portion 141A that is a distal end part on a side facing the first illumination window 90A. A distal end part of the light guide distal end portion 141A on the emission end side is inclined by the aforementioned first illumination axis angle θ1 with respect to a proximal end part of the light guide distal end portion 141A, which is parallel to the longitudinal axis LA.

The second light guide 128B has the light guide distal end portion 141B that is a distal end part on a side facing the second illumination window 90B. A distal end part of the light guide distal end portion 141B is inclined by the aforementioned second illumination axis angle θ2 with respect to a proximal end part of the light guide distal end portion 141B, which is parallel to the longitudinal axis LA.

Here, a metal member such as a mouthpiece is attached to the distal end part of each of the light guide distal end portions 141A and 141B. A proximal end part of each of the light guide distal end portions 141A and 141B is covered by a tube of various types.

When emitting illumination light from the emission ends thereof, the light guide distal end portions 141A and 141B generate heat by absorbing a part of the illumination light. Therefore, in the present embodiment, heat dissipation of the light guide distal end portions 141A and 141B is performed by using the elevating case 200.

As described above, in the upper surface of the outer wall of the base 202 of the elevating case 200, the two light guide holding grooves 203A and 203B (see FIGS. 5 and 6), each of which corresponds to a light guide holding portion and a groove according to the present invention, are formed.

The proximal end part of the light guide distal end portion 141A is fitted to the light guide holding groove 203A. Thus, the light guide holding groove 203A holds the light guide distal end portion 141A at a position such that the distal end part (emission end) thereof faces the first illumination window 90A. The proximal end part of the light guide distal end portion 141B is fitted to the light guide holding groove 203B. Thus, the light guide holding groove 203B holds the light guide distal end portion 141B at a position such that the distal end part (emission end) thereof faces the second illumination window 90B.

In order to further reduce the size of the distal end portion 50, the light guide distal end portions 141A and 141B may be fixed to the light guide holding grooves 203A and 203B by using an adhesive, without providing mouthpieces, tubes, and the like on the light guide distal end portions 141A and 141B.

The elevating case 200, which is made of a metal, has a higher thermal conductivity than the light guide distal end portions 141A and 141B. Heat is transferred from the light guide distal end portions 141A and 141B to the elevating case 200, because the elevating case 200 and the light guide distal end portions 141A and 141B are directly in contact with each other or are indirectly in contact with each other via metal members such as mouthpieces. Thus, it is possible to perform heat dissipation of the light guide distal end portions 141A and 141B.

When the outer case cover 72b (corresponding to a cover in the present invention), which is illustrated in the aforementioned FIGS. 3 to 5, is attached to the opening portion 71 of the outer case body 72a, the light guide distal end portions 141A and 141B are pressed by an inner surface of the outer case cover 72b toward an upper surface of the elevating case 200. Thus, by the outer case cover 72b, the light guide distal end portions 141A and 141B are pressed against the inside of the light guide holding grooves 203A and 203B and fixed. As a result, the heat dissipating ability of the light guide distal end portions 141A and 141B is improved, because the closeness of contact between the light guide distal end portions 141A and 141B and the elevating case 200 is improved. A pressing part, such as a projection, for pressing the light guide distal end portions 141A and 141B may be provided on the inner surface of the outer case cover 72b.

A metal pipe 145 is connected to the outer case proximal end side of the elevating case 200. The metal pipe 145 connects the treatment tool insertion channel 100 and the through hole 202a of the elevating case 200. Thus, the treatment tool insertion channel 100 and the elevator housing chamber 94a communicate with each other via the metal pipe 145 and the through hole 202a. Therefore, a treatment tool inserted through the inside of the treatment tool insertion channel 100 is guided to the elevator housing chamber 94a through the metal pipe 145 and the through hole 202a.

The metal pipe 145, which is made of a metal, has a higher thermal conductivity than the light guide distal end portions 141A and 141B. Therefore, it is possible to transfer heat generated in the light guide distal end portions 141A and 141B further to the metal pipe 145 via the elevating case 200. Thus, it is possible to further improve the heat dissipating ability of the light guide distal end portions 141A and 141B.

In the present embodiment, heat of the light guide distal end portions 141A and 141B is transferred to the bending portion 52 via the elevating case 200.

Figure 14:
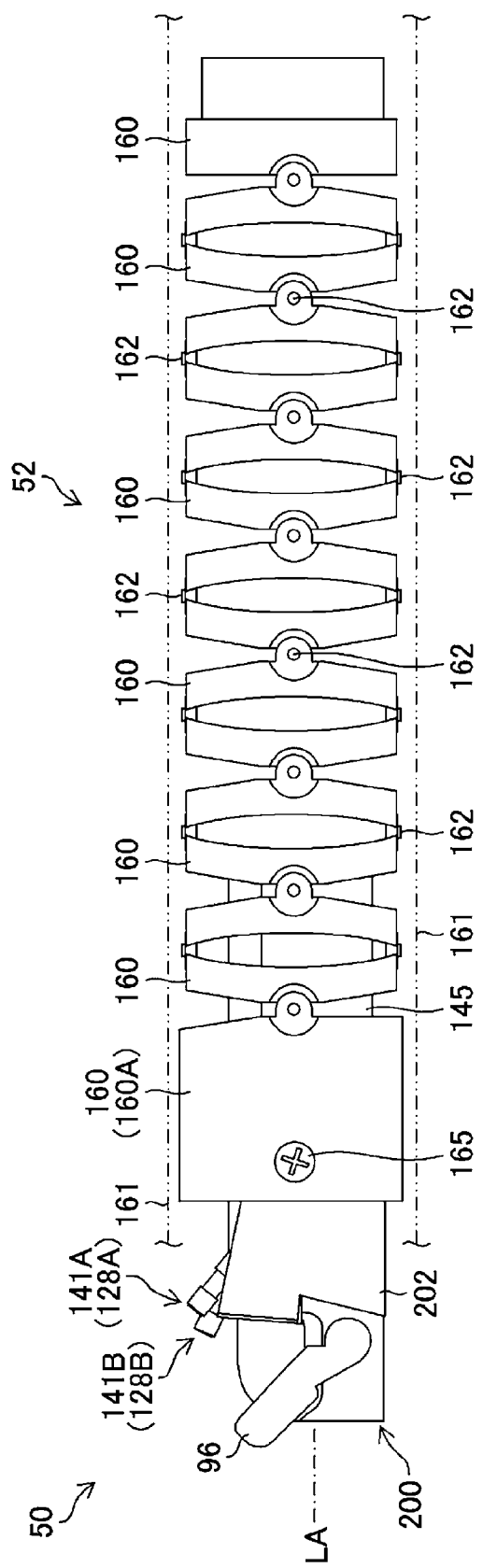
FIG. 14 is a schematic view of a bending portion.

FIG. 14 is a schematic view of the bending portion 52. As illustrated in FIG. 14, the bending portion 52 includes a plurality of rings 160 (also referred to as "nodal rings" or "bridges") that are made of a metal and that are coupled along the longitudinal axis LA, and a tube 161 that covers the rings 160. The rings 160 that are adjacent to each other are rotatably coupled via a crimp pin 162. Because the coupling structure of the rings 160 is a known technology, description of the details thereof will be omitted here.

Each of the rings 160, which is made of a metal, has a higher thermal conductivity than the light guide distal end portions 141A and 141B, as with the aforementioned elevating case 200 and the metal pipe 145.

A plurality of angle wires (not shown) are inserted through the inside of the rings 160. One end side of each of the angle wires is connected to the distal end portion 50, and other end side of each of the angle wires is coupled to a pulley (not shown) that is rotated by using the pair of angle knobs 42. Thus, the bending portion 52 is remotely operated to be bent (angle operation) by rotating the pair of angle knobs 42 of the operation section 22. As a result, it is possible to direct the distal end portion 50 in a desired direction.

A ring 160 that is positioned on the most distal end side (the distal end portion 50 side) of the bending portion 52 among the rings 160 (hereafter referred to as a "distal end ring 160A) is fixed to the outer case 72 in a state in which the distal end ring 160A is connected (coupled) to the outer case proximal end side of the outer case 72 by using a bolt (not shown) or the like.

At this time, a proximal end part of the base 202 of the elevating case 200 on the outer case proximal end side is inserted into the distal end ring 160A. The proximal end part of the base 202 is fixed to the inside of the distal end ring 160A by using a metal bolt 165 (corresponding to another metal member in the present invention) that extends through the distal end ring 160A from the outer peripheral side to the inner peripheral side thereof. Therefore, the elevating case 200 and the distal end ring 160A are indirectly connected to each other via the bolt 165. The elevating case 200 and the distal end ring 160A may be directly connected to each other by providing a holding portion that holds the proximal end part of the base 202, a contact portion that contacts the base 202, or the like in the distal end ring 160A.

Thus, by indirectly connecting the elevating case 200 and the distal end ring 160A via a metal member such as the bolt 165, by directly connecting these, or by using both of the indirect and direct connections, it is possible to transfer heat generated in the light guide distal end portions 141A and 141B to the distal end ring 160A and the other rings 160 via the elevating case 200. Thus, it is possible to further improve the heat dissipating ability of the light guide distal end portions 141A and 141B.

Advantageous Effects of Present Embodiment

As described above, with the present embodiment, the light guide distal end portions 141A and 141B are each held by the elevating case 200 made of a metal, and thereby it is possible to perform heat dissipation of the light guide distal end portions 141A and 141B by transferring heat generated in the light guide distal end portions 141A and 141B to the elevating case 200. Thus, increase in the temperature of the light guide distal end portions 141A and 141B can be suppressed without providing a heat insulator in the distal end portion 50. As a result, increase in the temperature of the distal end portion 50 can be suppressed while preventing increase in the number of components and increase in the diameter of the distal end portion 50.

Moreover, in the present embodiment, the metal pipe 145, the distal end ring 160A (the rings 160), and the like are connected to the elevating case 200, and thereby it is possible to transfer heat, which has been transferred from the light guide distal end portions 141A and 141B to the elevating case 200, further from the elevating case 200 to the metal pipe 145, the distal end ring 160A, and the like. As a result, it is possible to further improve the heat dissipating ability of the light guide distal end portions 141A and 141B.

Furthermore, with the present embodiment, because both of the illumination windows 90A and 90B are disposed in the ejection range of a fluid ejected from the air/water supply nozzle 92 (corresponding to a nozzle in the present invention), it is possible to cool the light guide distal end portions 141A and 141B via the illumination windows 90A and 90B by using the fluid ejected from the air/water supply nozzle 92. As a result, increase in the temperature of the light guide distal end portions 141A and 141B, that is, increase in the temperature of the distal end portion 50 can be suppressed.

[Ultrasonic Endoscopes According to Other Embodiments]

In the ultrasonic endoscope 10 according to the embodiment described above, the first illumination window 90A is disposed in the proximal end side region ER of the outer case 72. However, the first illumination window 90A may be disposed outside of the proximal end side region ER of the outer case 72.

Figure 15:
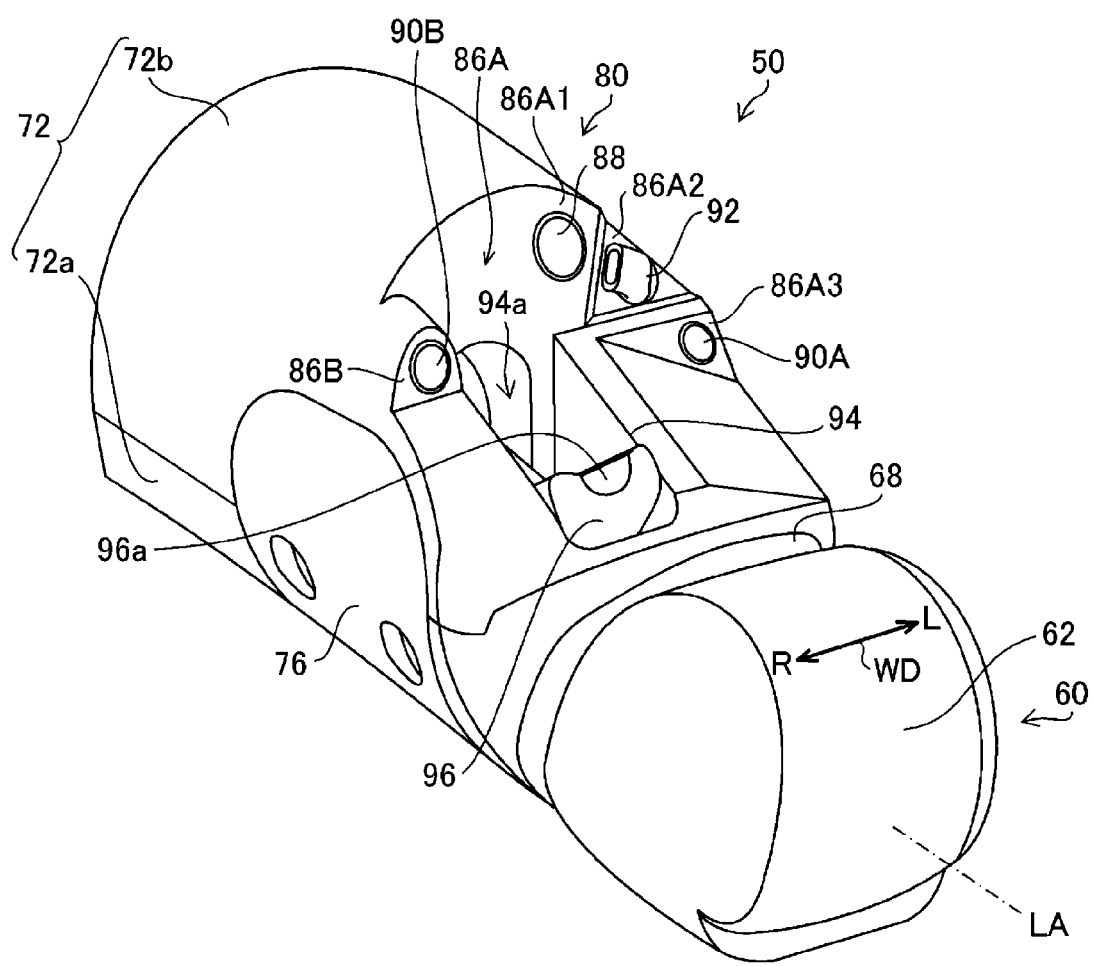
FIG. 15 is an external perspective view of a distal end portion of an ultrasonic endoscope according to another embodiment in which the disposition of the first illumination window is different.

FIG. 15 is an external perspective view of a distal end portion 50 of an ultrasonic endoscope 10 according to another embodiment in which the disposition of the first illumination window 90A is different. As illustrated in FIG. 15, the ultrasonic endoscope 10 according to the other embodiment basically has the same configuration as the ultrasonic endoscope 10 according to the embodiment described above, except for the following differences: the first inclined surface 86A of the outer case 72 has an observation window region 86A1, a nozzle region 86A2, and an illumination window region 86A3 that are parallel to each other; and the disposition of the first illumination window 90A in the outer case 72. Therefore, elements that are the same as those of the embodiment described above will be denoted by the same numerals and descriptions thereof will be omitted. Hereafter, a direction opposite to the normal direction of the first inclined surface 86A will be referred to as an "anti-normal direction".

The observation window region 86A1, the nozzle region 86A2, and the illumination window region 86A3 are each an inclined surface that constitutes a part of the first inclined surface 86A and that has the aforementioned first illumination axis 151A as a normal line. The observation window region 86A1 is formed in the first inclined surface 86A at a position that is on the outer case proximal end side relative to the treatment tool lead-out port 94 in the direction along the longitudinal axis LA and that is on the L side relative to the treatment tool lead-out port 94 in the width direction WD. The aforementioned observation window 88 is provided in the observation window region 86A1.

The nozzle region 86A2 is formed in the first inclined surface 86A at a position that is on the anti-normal side relative to the observation window region 86A1 and that is on the L side relative to the observation window region 86A1 in the width direction WD. The nozzle region 86A2 is shifted furthest toward the anti-normal side in the first inclined surface 86A. The aforementioned air/water supply nozzle 92 is provided in the nozzle region 86A2.

The illumination window region 86A3 is formed in the first inclined surface 86A at a position that is on the normal side of the first inclined surface 86A relative to the tip of the air/water supply nozzle 92 and that is on the L side relative to the treatment tool lead-out port 94 in the width direction WD. The illumination window region 86A3 is shifted furthest toward the normal side of the first inclined surface 86A in the first inclined surface 86A. The first illumination window 90A according to the other embodiment is formed in the illumination window region 86A3.

As in the embodiment described above, according to the other embodiment, the first illumination window 90A (the first illumination axis 151A and the first illumination range 151B) is inclined toward the outer case proximal end side by the difference Δθ relative to the second illumination window 90B (the second illumination axis 152A and the second illumination range 152B). Thus, the first illumination window 90A can illuminate a treatment tool and a treatment target area thereof with illumination light.

At this time, the first illumination window 90A according to the other embodiment is provided in the aforementioned illumination window region 86A3, that is, at a position on the L side relative to the elevating case 200 in the width direction WD. Therefore, in the other embodiment, the first light guide 128A is disposed in the outer case 72 not on the upper surface of the base 202 but at a position separated from the base 202 toward the L side. Thus, in the other embodiment, only the light guide distal end portion 141B of the second light guide 128B is held by the elevating case 200. Accordingly, in the other embodiment, the second light guide 128B corresponds to a light guide in the present invention, and the second illumination window 90B corresponds to an illumination window in the present invention.

Figure 16:
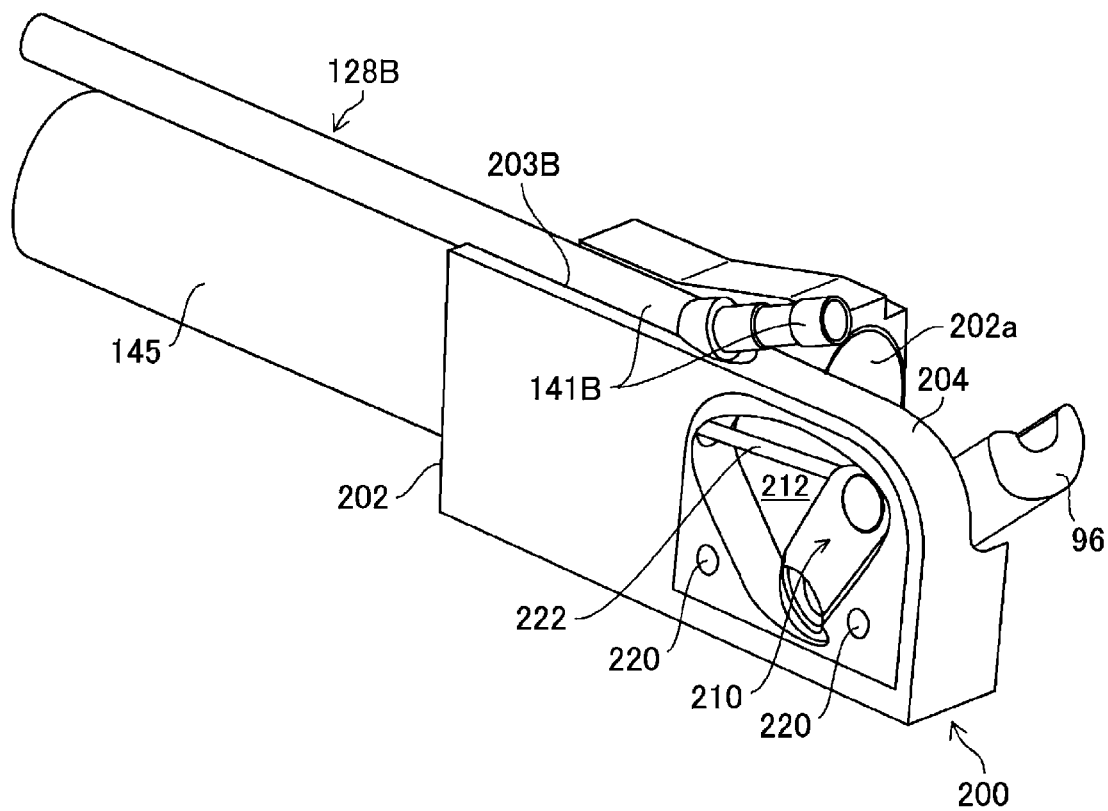
FIG. 16 is a perspective view of an elevating case according to another embodiment and a second light guide held by the elevating case.

FIG. 16 is a perspective view of an elevating case 200 according to another embodiment and the second light guide 128B held by the elevating case 200. As illustrated in FIG. 16, the elevating case 200 according to the other embodiment has basically the same structure as the elevating case 200 according to the embodiment described above, except that only the light guide holding groove 203B is formed in the upper surface thereof and the light guide distal end portion 141B is held by the light guide holding groove 203B. Thus, with the other embodiment, it is possible to transfer heat generated in the light guide distal end portion 141B to the elevating case 200 and to further transfer the heat via the elevating case 200 to the metal pipe 145, the distal end ring 160A (the rings 160), and the like.

In this way, with the other embodiment, it is possible to suppress increase in the temperature of the light guide distal end portion 141B, because heat dissipation of the light guide distal end portion 141B is performed by using the elevating case 200 made of a metal. As a result, with the other embodiment, increase in the temperature of the distal end portion 50 can be suppressed, compared with a case where the temperatures of both of the light guide distal end portions 141A and 141B increase as in existing endoscopes. Thus, because it is not necessary to provide a heat insulator and the like in the distal end portion 50, increase in the number of components and increase in the diameter of the distal end portion 50 is prevented.

In the other embodiment described above, the observation window region 86A1, the nozzle region 86A2, and the illumination window region 86A3, which differ from each other, are formed in the first inclined surface 86A. However, the observation window region 86A1, the nozzle region 86A2, and the illumination window region 86A3 may be formed in the same plane that does not have a step. In the other embodiment described above, the observation window region 86A1 (the observation axis 150A) and the illumination window region 86A3 (the first illumination axis 151A) in the first inclined surface 86A are formed to be parallel. However, these regions may be formed not to be parallel. Moreover, the first illumination window 90A may be omitted, provided that, for example, the aforementioned forward visibility and the visibility of the treatment tool and the treatment target area can be reliably obtained by using only the second illumination window 90B.

OTHERS

In the embodiment described above, the light guide holding grooves 203A and 203B are formed in the upper surface of the outer wall the elevating case 200 (the base 202).

However, the light guide holding grooves 203A and 203B may be formed in a surface other than the upper surface of the outer wall.

Figure 17:
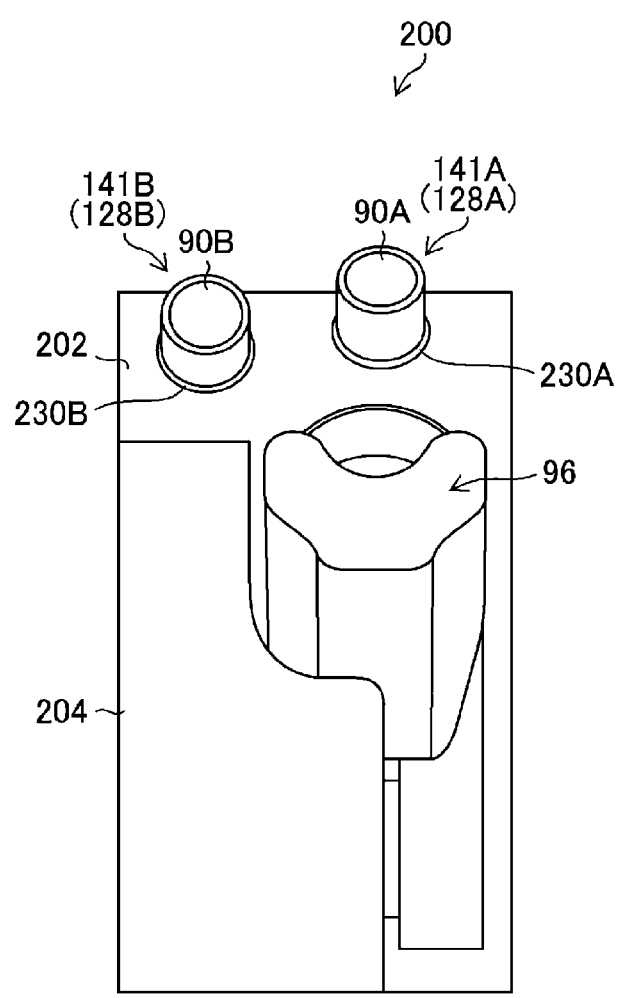
FIG. 17 illustrates another example of a holding structure of an elevating case for holding light guide distal end portions.

FIG. 17 illustrates another example of a holding structure of an elevating case 200 for holding the light guide distal end portions 141A and 141B. In the embodiment described above, the light guide distal end portions 141A and 141B are held by the light guide holding grooves 203A and 203B formed in the upper surface of the elevating case 200. However, the light guide distal end portions 141A and 141B may be held by using another means.

As illustrated in FIG. 17, as a light guide holding portion in the present invention, two through holes 230A and 230B (or tubes) may be provided in a base 202 of the elevating case 200 so as to extend from a distal end surface on the outer case distal end side thereof to a proximal end surface on the outer case proximal end side thereof. The light guide distal end portion 141A is inserted through the inside of the through hole 230A and fixed, and the light guide distal end portion 141B is inserted through the inside of the through hole 230B and fixed. Thus, heat generated in the light guide distal end portions 141A and 141B can be transferred to the elevating case 200, and advantageous effects that are the same as those of the embodiment described above can be obtained. Also in the other embodiment illustrated in FIG. 16, the through hole 230B may be formed in the base 202 of the elevating case 200.

A light guide holding portion in the present invention is not particularly limited, provided that the light guide holding portion has a structure that holds the light guide distal end portions 141A and 141B and that can transfer heat of the light guide distal end portions 141A and 141B to the elevating case 200.

In the embodiment described above, an example in which the elevator 96 is rotated via the operating wire 222 and the elevator elevating lever 210 is described. However, a method for rotating the elevator 96 is not particularly limited, and a known method can be used.

In the embodiment described above, the first inclined surface 86A, the observation window 88, and the first illumination window 90A are parallel. However, the observation window 88 and the first illumination window 90A may not be parallel to the first inclined surface 86A. Likewise, the second illumination window 90B may not be parallel to the second inclined surface 86B.

In the embodiment described above, the ultrasonic endoscope 10 that includes the ultrasonic observation portion 60 (the ultrasonic transducer 62) has been described as an example. However, the present invention is applicable to any endoscope that includes the elevator 96 for guiding a treatment tool, for example, a side-viewing endoscope such as a duodenoscope.

REFERENCE SIGNS LIST 2 ultrasonic inspection system
10 ultrasonic endoscope
12 ultrasonic processor device
14 endoscopic processor device
16 light source device
18 monitor
20 insertion section
22 operating unit
24 universal cord
27 ultrasonic connector
28 endoscopic connector
30 light source connector 32 tube
34 tube
36 air/water supply button
38 suction button
42 angle knob
43 operating lever
44 treatment tool insertion port
50 distal end portion
52 bending portion
54 soft portion
60 ultrasonic observation portion
62 ultrasonic transducer
64 balloon
66 locking ring
68 locking groove
70 supply/discharge port
71 opening portion
72 outer case
72a outer case body
72b outer case cover
73 partition wall
74 groove portion
75 fitting hole
76 lever housing cover
77 bolt
80 endoscope observation portion
86A first inclined surface
86A1 observation window region
86A2 nozzle region
86A3 illumination window region
86B second inclined surface
88 observation window
90A first illumination window
90B second illumination window
92 air/water supply nozzle
94 treatment tool lead-out port
94a elevator housing chamber
96 elevator
96a guide surface
100 treatment tool insertion channel
102 air/water supply pipe line
104 balloon pipe line
106 suction pipe line
108 air supply pipe line
110 water supply pipe line
112 balloon water supply pipe line
114 balloon water discharge pipe line
116 air supply source pipe line
118 water supply tank
120 water supply source pipe line
122 branch pipe line
124 suction pump
126 suction source pipe line
128 light guide
128A first light guide
128B second light guide
129 air supply pump
141A light guide distal end portion
141B light guide distal end portion
145 metal pipe
150A observation axis
150B observation range
151A first illumination axis
151B first illumination range
152A second illumination axis
152B second illumination range
154 lumen
160 ring
160A distal end ring
161 tube
162 crimp pin
165 bolt
200 elevating case
202 base
202a through-hole
203A light guide holding groove
203B light guide holding groove
204 partition wall
206 side wall
208 counter wall
208a cutout portion
210 elevator elevating lever
211 bolt
212 lever housing
214 holding hole
216 rotation shaft
220 bolt hole
222 operating wire
222a distal end side coupling portion
222b proximal end side coupling portion
224 wire insertion hole
226 elevator operating mechanism
226A rotary drum
226B crank member
226C slider
230A through-hole
230B through-hole
ER proximal end side region
LA longitudinal axis
LB reference axis
NV normal direction
WD width direction
Δθ difference
θ0 observation axis angle
θ1 first illumination axis angle
θ2 second illumination axis angle

What is claimed is:

1. An endoscope comprising:
a distal end portion body that is provided on a distal end side of an insertion section;
a treatment tool lead-out port that is formed in the distal end portion body and that has an opening surface from which a treatment tool inserted through an inside of the insertion section is led out;
an elevator that controls a lead-out direction in which the treatment tool is led out from the opening surface of the treatment tool lead-out port;
an elevator support member that is provided in the distal end portion body, that is made of a metal, and that houses an elevator elevating lever that is coupled to the elevator via a rotation shaft, the rotation shaft being configured to rotate around an axis of the rotation shaft, the axis of the rotation shaft being perpendicular to a longitudinal axis of the distal end portion body;
a light guide that is inserted through the inside of the insertion section and that emits illumination light through an illumination window formed in the distal end portion body; and
a light guide holding portion that is provided in the elevator support member and that holds a light guide distal end portion of the light guide on the illumination window side, wherein the elevator elevating lever is configured to rotate at least toward and away from the light guide holding portion, and when the elevator elevating lever is rotated toward the light guide holding portion, and a plane of rotation of the elevator elevating lever intersects with the light guide holding portion, and the plane of rotation is normal to the axis of the rotation shaft and passes through the elevator.

2. The endoscope according to claim 1, wherein the light guide holding portion is a groove that is formed in an outer wall of the elevator support member and to which the light guide distal end portion is fitted.

3. The endoscope according to claim 2,
wherein the distal end portion body comprises an outer case including an outer case body and a cover,
wherein the outer case body has an opening portion and houses the elevator support member and the elevator in the opening portion, and
wherein the cover is removably attached to the opening portion and, when attached to the opening portion, presses the light guide distal end portion, which is fitted to the groove, against the groove and fixes the light guide distal end portion.

4. The endoscope according to claim 1, comprising:
an elevator housing chamber that is provided inside the treatment tool lead-out port of the distal end portion body and that houses the elevator;
a treatment tool insertion channel that is provided in the insertion section and through which the treatment tool is inserted;
a through hole that is formed in the elevator support member and that communicates with the elevator housing chamber; and
a metal pipe that connects the treatment tool insertion channel and the through hole of the elevator support member.

5. The endoscope according to claim 1, comprising:
a bending portion that is connected to a proximal end side of the distal end portion body in the insertion section,
wherein the bending portion has a plurality of rings that are made of a metal and that are coupled along the longitudinal axis, and
wherein the elevator support member is connected directly or indirectly via another metal member to a distal end ring that is positioned on a most distal end side of the bending portion among the plurality of rings.

6. The endoscope according to claim 1, comprising
an observation window that is provided in the distal end portion body; and
a nozzle that is provided in the distal end portion body and that ejects a fluid toward the observation window,
wherein the illumination window is provided, in the distal end portion body, in an ejection range of the fluid ejected from the nozzle.

7. The endoscope according to claim 6,
wherein, when the first direction is defined as a width direction of the treatment tool lead-out port, the observation window is provided in the distal end portion body at a position on one side in the width direction relative to the treatment tool lead-out port, and
wherein the illumination window is provided in the distal end portion body at a position on the other side, which is opposite to the one side, relative to the treatment tool lead-out port.

8. The endoscope according to claim 6,
wherein the illumination window is a first illumination window that is provided in a proximal end side region that is positioned in the distal end portion body at a position shifted from the treatment tool lead-out port toward a proximal end side of the distal end portion body, and
wherein, when a direction perpendicular to both of the longitudinal axis and a normal direction of an opening surface of the treatment tool lead-out port is defined as a width direction of the treatment tool lead-out port, the observation window is provided in the distal end portion body at a position on one side in the width direction with respect to the proximal end side region.

9. The endoscope according to claim 8, wherein the illumination window includes the first illumination window and a second illumination window that is disposed in the distal end portion body at a position on the other side, which is opposite to the one side, with respect to the proximal end side region.

10. The endoscope according to claim 1, comprising an ultrasonic transducer that is provided in the distal end portion body and that is positioned on a distal end side of the distal end portion body relative to the treatment tool lead-out port.

* * * * *